United States Patent [19]

Bonham

[11] Patent Number: 5,484,919
[45] Date of Patent: Jan. 16, 1996

[54] MIGRATION-RESISTANT HALOMETHYL-1,3,5-TRIAZINE PHOTOINITIATOR

[75] Inventor: James A. Bonham, Grant Township, Minn.

[73] Assignee: Minnesota Mining and Manufacturing Company, Saint Paul, Minn.

[21] Appl. No.: 189,927

[22] Filed: Feb. 1, 1994

Related U.S. Application Data

[62] Division of Ser. No. 752,775, Aug. 30, 1991, Pat. No. 5,298,361.

[51] Int. Cl.$^6$ ................................................ C07D 251/24
[52] U.S. Cl. .................................... 544/193.1; 544/193.2; 544/215
[58] Field of Search ........................... 544/193.1, 193.2, 544/215

[56] References Cited

U.S. PATENT DOCUMENTS

| | | | |
|---|---|---|---|
| 3,376,136 | 4/1968 | Seide | 522/904 X |
| 3,617,288 | 11/1971 | Hartman et al. | 96/90 |
| 3,671,236 | 3/1968 | Van Beusekom | 96/15 |
| 3,884,693 | 5/1975 | Bauer et al. | 96/15 |
| 3,954,475 | 5/1976 | Bonham et al. | 96/67 |
| 3,987,037 | 10/1976 | Bonham et al. | 522/63 X |
| 4,174,216 | 11/1979 | Cohen et al. | 430/257 |
| 4,189,323 | 2/1980 | Buhr | 430/281 X |
| 4,200,762 | 4/1980 | Schmidle | 560/26 |
| 4,304,923 | 12/1981 | Rousseau | 560/26 |
| 4,408,532 | 10/1983 | Incremona | 101/456 |
| 4,476,215 | 10/1984 | Kausch | 430/281 |
| 4,596,757 | 6/1986 | Barton et al. | 430/257 |
| 4,619,998 | 10/1986 | Buhr | 544/193.1 |
| 4,696,888 | 9/1987 | Buhr | 522/63 X |
| 4,772,534 | 9/1988 | Kawamura et al. | 430/176 |
| 4,806,451 | 2/1989 | Frohlich | 430/291 |
| 4,820,607 | 4/1989 | Aoai | 522/63 X |
| 4,826,753 | 5/1989 | Higashi et al. | 522/63 X |
| 4,837,128 | 6/1989 | Kawamura et al. | 522/63 X |
| 4,855,384 | 8/1989 | Larson | 528/60 |
| 4,923,780 | 5/1990 | Taylor, Jr. | 430/258 |
| 4,933,452 | 6/1990 | White et al. | 544/204 |
| 4,950,795 | 8/1990 | Husler et al. | 522/904 X |
| 4,985,562 | 1/1991 | Rossman et al. | 544/244 |
| 4,997,745 | 3/1991 | Kawamura et al. | 430/281 |
| 5,248,583 | 9/1993 | Lundquist et al. | 430/263 |

OTHER PUBLICATIONS

*Encyclopedia of Polymer Science and Engineering*, John Wiley & Sons, (New York, 1987), vol. 8, pp. 450–452.
A. Hassner and V. Alexanian, *Tetrahedron Letters*, No. 46, pp. 4475–4478, 1978 (Pergamon Press Ltd., United Kingdom).

Primary Examiner—Yogendra N. Gupta
Attorney, Agent, or Firm—Gary L. Griswold; Walter N. Kirn; David L. Weinstein

[57] ABSTRACT

A chromophore-substituted halomethyl-1,3,5-triazine photopolymerization initiator. The initiator preferably comprises three moieties—a residue of a hydroxyl-substituted, chromophore-substituted, halomethyl-1,3,5-triazine compound; a residue of a diisocyanate compound having isocyanato groups of dissimilar reactivities; a residue of a hydroxyl-substituted compound, e.g., the residue of a polyoxyethylene alkylphenol.

14 Claims, No Drawings

MIGRATION-RESISTANT HALOMETHYL-1,3,5-TRIAZINE PHOTOINITIATOR

This is a division of application Ser. No. 07/752,775 filed Aug. 30, 1991 U.S. Pat. No. 5,298,361.

BACKGROUND OF THE INVENTION

1. Field of the Invention

This invention relates to a multilayer, light-sensitive article having (a) a layer containing a photopolymerizable material containing a photopolymerization initiator and a polymerizable ethylenically unsaturated compound, and (b) a layer containing a thermoplastic resin. More specifically, the invention relates to multilayer, light-sensitive articles containing halomethyl-1,3,5-triazine photopolymerization initiators that resist migration from the layer of photopolymerizable material to layers adjacent thereto.

2. Description of the Prior Art

Light-sensitive articles comprising a photopolymerizable layer containing a polymerizable ethylenically unsaturated compound and a photopolymerization initiator are well known in the graphic arts. The purpose of the photopolymerization initiator, alternatively referred to herein as "photoinitiator", is to generate free radicals upon imagewise exposure of the polymerizable layer to actinic radiation to initiate polymerization of the ethylenically unsaturated compound to produce an image. One common method of developing such an image utilizes the solubility differential created between the material in less soluble (exposed) region and the material in the more soluble (unexposed) region by removal of the latter material with an appropriate solvent. Another common method of developing such an image utilizes a laminate in which the material in the photopolymerized (exposed) region preferentially adheres to one of the layers in the laminate and can be separated from the material in the unpolymerized (unexposed) region by peeling the laminate apart. A general review of photopolymerization and development techniques is described in C. G. Roffey, *Photopolymerization of Surface Coatings*, John Wiley and Sons (New York, 1982), Chapters 4 and 6.

Light-sensitive articles have been employed in the preparation of overlay or surprint color proofing sheets, which are used to verify the accuracy, with respect to color, of separation films used in the preparation of printing plates. For example, a single-sheet, four-color proof (surprint) must duplicate with great accuracy the colored image and background to be achieved on a printing press using printing plates made with the same separation films. Processes and methods of color proofing are described in M. H. Bruno, *Principles of Color Proofing*, Gama Communications (Salem, N.H., 1986).

Whenever a layer of a photopolymerizable material that is a component of a proofing sheet construction comes into contact with a layer of resin, it is possible for one or more colored components of the layer of photopolymerizable material to migrate into the layer of resin and bring about a discoloration in that layer. For example, U.S. Pat. No. 4,596,757 describes a process that utilizes a photographic element having a substrate and sequentially carried thereon three layers which are a release layer, a colored photohardenable layer, and an adhesive layer. The process of the patent allows the operator to halve a choice of two image formation methods using the same composite photographic element. These choices are full colored layer transfer with subsequent sequential image formation, and individual image formation with image only superimposition.

1. If an image only transfer is desired, the operator may expose the composite through a negative flat placed in contact, emulsion to adhesive. The resulting latent image film is then transferred to a temporary receiving sheet, preferably a polyester film, before developing the image with the developer solution. Each color in the four color transfer process is likewise exposed and transferred to its own polyester sheet and the image developed. As a last step, the image may be transferred in register to given right reading image.

2. If a full solid color layer transfer is preferred, a first coated composite is transferred to a permanent base and is then exposed with subsequent development of the image. This is a sequential color transfer process and each of the subsequent colors must be transferred on top of the previous color, exposed in register and developed to obtain the full four-color proof.

In either method, one or more adhesive layers remain superimposed in the background (i.e., the unexposed and developed areas), the particular number of layers depending on the number of color images superimposed on the receptor sheet. The migration of one or more components of the layer of photopolymerizable material into the contiguous resin layer generally results in a discolored background and an unsatisfactory proof.

Other examples of proofing constructions in which the layer of photopolymerizable material comes into contact with a layer of resin are described in U.S. Pat. Nos. 3,884,693; 4,174,216; 4,806,451; and 4,923,780.

Examples of light-sensitive compounds that initiate photopolymerization by decomposing to generate free radicals upon exposure to light are well known and have been described in C. G. Roffey, *Photopolymerization of Surface Coatings*, John Wiley and Sons (New York, 1982), Chapter 3. Chromophore-substituted halomethyl-1,3,5-triazine compounds are a particularly effective class of photopolymerization initiators. These triazine compounds respond to radiation in the near ultraviolet to visible light region. For example, U.S. Pat. Nos. 3,954,475; 3,987,037; 4,189,323; 4,696,888; 4,772,534; 4,826,753; and 4,837,128 disclose such chromophore-substituted halomethyl-1,3,5-triazine compounds. However, in the multilayer, light-sensitive articles previously described, these compounds were found to migrate out of the layer of photopolymerizable material to produce a discoloration in the background layer. U.S. Pat. No. 4,933,452 discloses triazine derivatives of polymeric or oligomeric compounds having a reduced tendency for migration. Unlike chromophore-substituted triazine compounds, these triazine compounds require that a separate sensitizing dye be incorporated in the layer of photopolymerizable material to be responsive to the radiation of the light sources used in graphic arts. The sensitizing dye used in the examples of U.S. Pat. No. 4,933,452, ethyl Michler's ketone, is known to migrate out of the layer 5f photopolymerizable material into a contiguous resin layer and cause a discoloration of the background.

Accordingly, it would be desirable to develop halomethyl-1,3,5-triazine compounds that resist migration from the layer of photopolymerizable material of a multilayer, light-sensitive article in order to overcome the problem of discoloration of the background.

SUMMARY OF THE INVENTION

This invention provides a light-sensitive article comprising (a) at least one layer of photopolymerizable material containing a polymerizable compound having at least one ethylenically unsaturated group, and a chromophore-substituted halomethyl-1,3,5-triazine photopolymerization initiator; (b) at least one layer of thermoplastic resin in contact with the layer of photopolymerizable material, said chromophore-substituted 1,3,5-triazine photopolymerization initiator capable of resisting migration to said layer of thermoplastic resin.

The preferred chromophore-substituted halomethyl-1,3,5-triazine photopolymerization initiator comprises three moieties—a residue of a hydroxyl-substituted, chromophore-substituted, halomethyl-1,3,5-triazine compound; a residue of a diisocyanate compound having isocyanato groups of dissimilar reactivities; a residue of a hydroxyl-substituted compound, e.g., the residue of a polyoxyethylene alkylphenol. The photopolymerization initiator typically comprises from about 1 to about 25% by eight of the layer of photopolymerizable material. The layer of photopolymerizable material can also contain a binder and a colorant, e.g., a pigment or a dye.

The invention eliminates the problem of discoloration of the background resulting from excessive migration of the photoinitiator from the layer of photopolymerizable material to the contiguous layer of resin. The invention is especially useful in the preparation of surprint color proofs.

In another aspect of this invention, this invention provides new chromophore-substituted halomethyl-1,3,5-triazine compounds and methods of preparing them.

DETAILED DESCRIPTION OF THE INVENTION

This invention provides a light-sensitive article comprising:

(a) at least one layer of photopolymerizable material containing a polymerizable compound having at least one ethylenically unsaturated group, and a chromophore-substituted halomethyl-1,3,5-triazine photopolymerization initiator; and (b) at least one layer of thermoplastic resin in contact with the layer of photopolymerizable material, said chromophore-substituted 1,3,5-triazine photopolymerization initiator capable of resisting migration to said layer of thermoplastic resin.

As used herein, the phrase "capable of resisting migration" means capable of remaining in the layer of photopolymerizable material so that formation 6f a visually observable discoloration in the background area of a surprint proof that is prepared from the article of this invention is prevented. The phrase "chromophore-substituted" means substituted by a chromophoric moiety conjugated with the triazine ring by ethylenic unsaturation, as described in U.S. Pat. No. 3,987,037, incorporated herein by reference.

The halomethyl-1,3,5-triazine photopolymerization initiator can have one of the following general formulae:

$$R^3 \text{---} \left[ \text{---} \underset{\text{O}}{\overset{\text{O}}{\text{OCHN}}} \text{---} R^2 \text{---} \underset{\text{O}}{\overset{\text{O}}{\text{NHCO}}} \text{---} R^1 \right]_x \quad \text{I}$$

wherein
$R^1$ represents a residue of a hydroxyl-substituted, chromophore-substituted, halomethyl-1,3,5-triazine compound, $R^1$—OH,
$R^2$ represents a residue from a compound, $R^2(NCO)_2$, having isocyanato groups, (NCO), of dissimilar reactivities, i.e., dissimilar rates of reaction $R^3$ represents a residue of a hydroxyl-substituted compound, $R^3(OH)_x$, where x represents an integer greater than or equal to 1, preferably 1 to 10;

$$R^4 \text{---} \left[ \text{---} \underset{\text{O}}{\overset{\text{O}}{\text{NHCO}}} \text{---} R^1 \right]_y \quad \text{II}$$

wherein
$R^1$ is as described previously,
$R^4$ represents a residue of a isocyanato compound, $R^4(NCO)_y$, where y represents an integer greater than or equal to 2, preferably 2 to 10;

$$R^5 \text{---} \left[ \text{---} \underset{\text{O}}{\overset{\text{O}}{\text{CO}}} \text{---} R^1 \right]_w \quad \text{III}$$

wherein
$R^1$ is as described previously,
$R^5$ represents a residue of a carboxylic acid $R^5(CO_2H)_w$, where w represents an integer greater than or equal to 2, preferably 2 to 10.

Examples of compounds having the formula $R^1$—OH that are particularly useful in the preparation of the compounds useful in this invention have the general Formula IV:

$$H \text{---} \left[ \text{---} \underset{R^6}{\text{OCHCH}_2} \text{---} \right]_m \text{---} O \text{---} A \quad \text{IV}$$

wherein m represents an integer from 0 to 10, $R^6$ represents a hydrogen atom or a methyl group, and A represents a chromophore-substituted halomethyl-1,3,5-triazine residue capable of absorbing light having a wavelength greater than 330 nm and preferably having a πmax greater than 330 nm. The moiety A is preferably selected from moieties having the generic Formulae V–VIII shown below, wherein X represents Cl or Br, n represents 1 or 2, and Ar represents an arylene group having up to 3 fused rings.

Particularly useful examples of the chromophore-substituted triazine residue $R^1$ are described in U.S. Pat. Nos. 3,987,037; 4,476,215; 4,826,753, incorporated herein by reference:

<chemical structure V> in U.S. Pat. Nos. 4,619,998; 4,696,888; and DE 3,517,440, incorporated herein by reference:

<chemical structure VI> in U.S. Pat. No. 4,772,534, incorporated herein by reference:

<chemical structure VII> and in U.S. Pat. Nos. 4,189,323; 4,837,128, incorporated herein by reference:

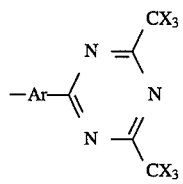

Based on ease of synthesis and performance, $R^1$—OH compounds preferred for this invention are selected from the chromophore-substituted vinyl triazine compounds of Formula IV wherein X represents Cl, m represents 0 or 1, A represents the triazine residue of Formula V, and n represents 1.

Examples of compounds having the formula $R^2(NCO)_2$ that are particularly useful in the preparation of the compounds of Formula I that are useful in this invention are tolylene-2,4-diisocyanate and isophorone diisocyanate.

Examples of compounds having the formula $R^3(OH)_x$ that are particularly useful in the preparation of the compounds of Formula I that are useful in this invention include (1) aliphatic alcohols and aliphatic polyols having from 1 to 20 carbon atoms; aralkyl alcohols and aralkyl polyols having up to 3 aromatic rings in the aryl portion thereof, and from 1 to 10 carbon atoms in the alkyl portion thereof; alkyl alcohols or alkyl polyols derived from heteroaromatic or heterocyclic compounds having from 1 to 10 carbon atoms in the alkyl portion thereof, e.g., 2-(2-hydroxyethyl)pyridine, 4-(2-hydroxyethyl)-1-piperazinepropanesulfonic acid; 2-(2-thienyl)ethanol, 3-benzyl-5-(2-hydroxyethyl)-4-methylthiazolium chloride; (2) polyoxyethylene compounds selected from the group consisting of polyoxyethylene alkylphenols, polyoxyethylene alcohols, polyoxyethylene esters, polyoxyethylene alkylamines, polyoxyethylene alkylamides, block copolymers of polyoxyethylene and polyoxypropylene; (3) polyoxypropylene compounds selected from the group consisting of polyoxypropylene alkylphenols, polyoxypropylene alcohols, polyoxypropylene esters, polyoxypropylene alkylamines, polyoxypropylene alkylamides, block copolymers of polyoxypropylene and polyoxyethylene; and (4) glycols selected from the group consisting of polyethylene glycols, polypropylene glycols, polycaprolactone diols, acetylenic glycols, adducts of acetylenic glycol and ethylene oxide, and sulfopolyols, such as those described in U.S. Pat. Nos. 4,855,384 and 4,408,532.

The hydroxyl compounds $R^3(OH)_x$ that are most preferred for this invention are selected from the derivatives of polyoxyethylene compounds or polyoxypropylene compounds, or both, and, of these compounds, the most preferred are those considered to be surface-active condensation products of polyoxyethylene. A thorough description of these compounds can be found in the *Nonionic Surfactants*, Vol. 1 (1967), Chapters 1–12; *Cationic Surfactants Organic Chemistry*, Vol. 34 (1990), Chapters 1–2; and *Alkylene Oxides and Their Polymers*, Vol. 35 (1990), Surfactant Science Series, Marcel Dekker, Inc. (New York). Many of these compounds are commercially available and are described in *McCutcheons* 1991, Volume 1, *Emulsifiers & Detergents*, and Volume 2, *Functional Materials*, MC Publishing Company (Glen Rock, N.J.), 1991. As a general guideline, polyoxyethylene compounds and polyoxypropylene compounds having from 1 to 100 oxyalkylene groups per chromophore-substituted triazine unit are preferred. Most preferred are those having from 1 to 25 oxyalkylene units per chromophore-substituted triazine unit.

Representative examples of the moiety $R^3$ of the compounds of Formula I are listed in Table 1.

TABLE 1

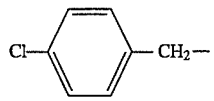

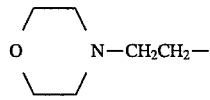

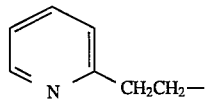

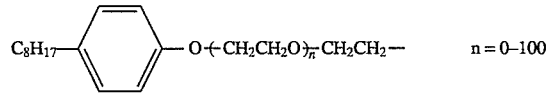     n = 0–100

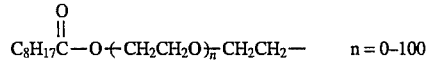     n = 0–100

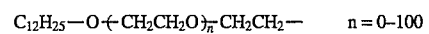     n = 0–100

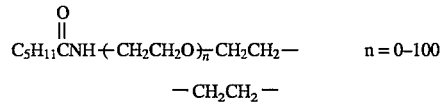     n = 0–100

—CH₂CH₂—

TABLE 1-continued
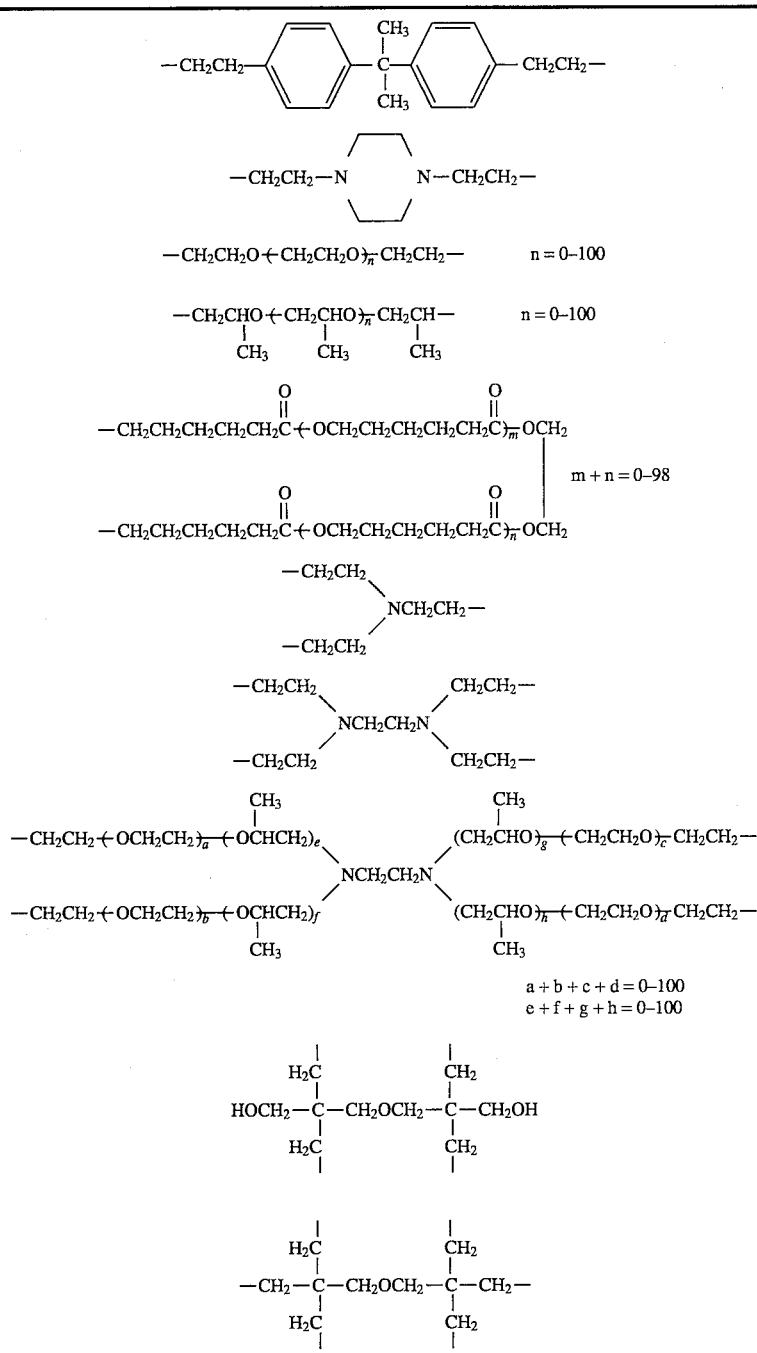
Representative examples of the moiety —O$_2$CHN—R$^2$—NHCO$_2$—R$^1$ of the compounds of Formula I are listed in Table 2.

TABLE 2
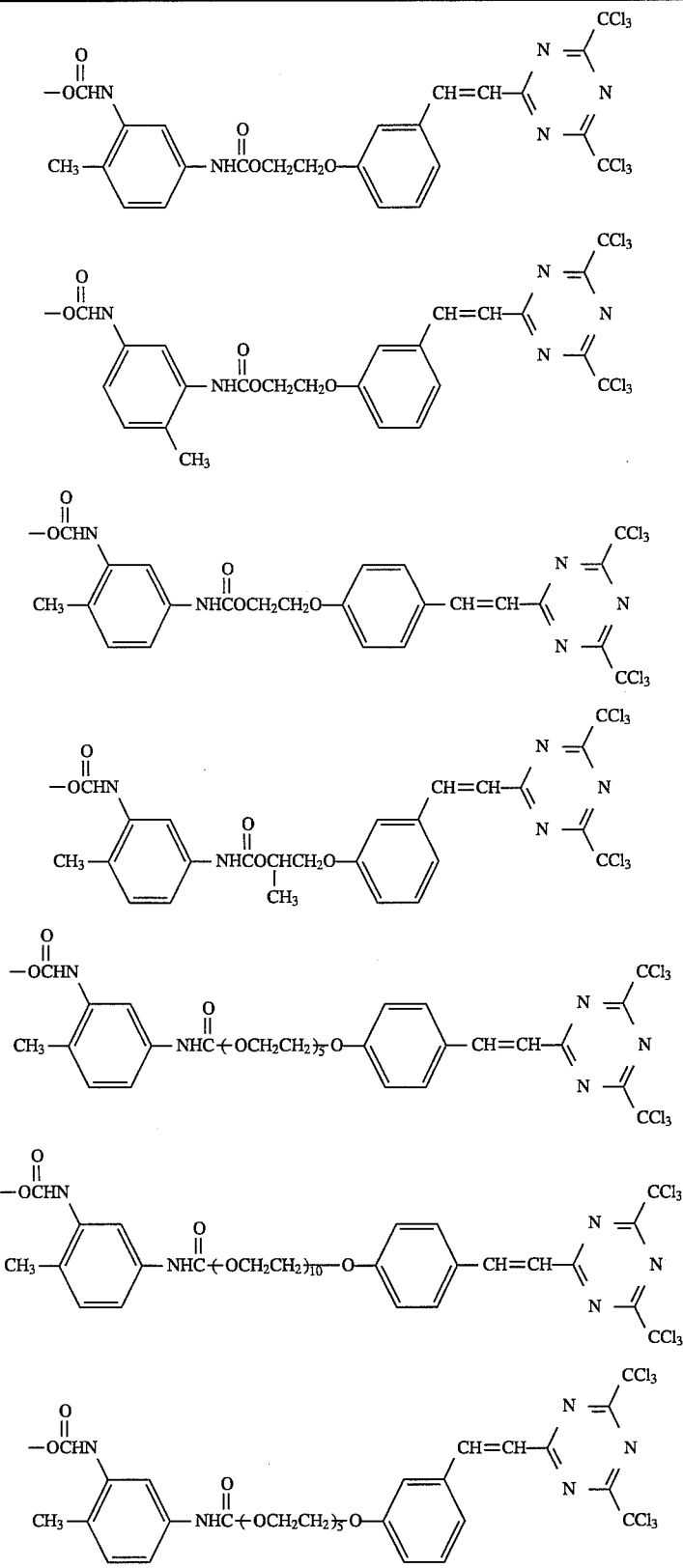

TABLE 2-continued

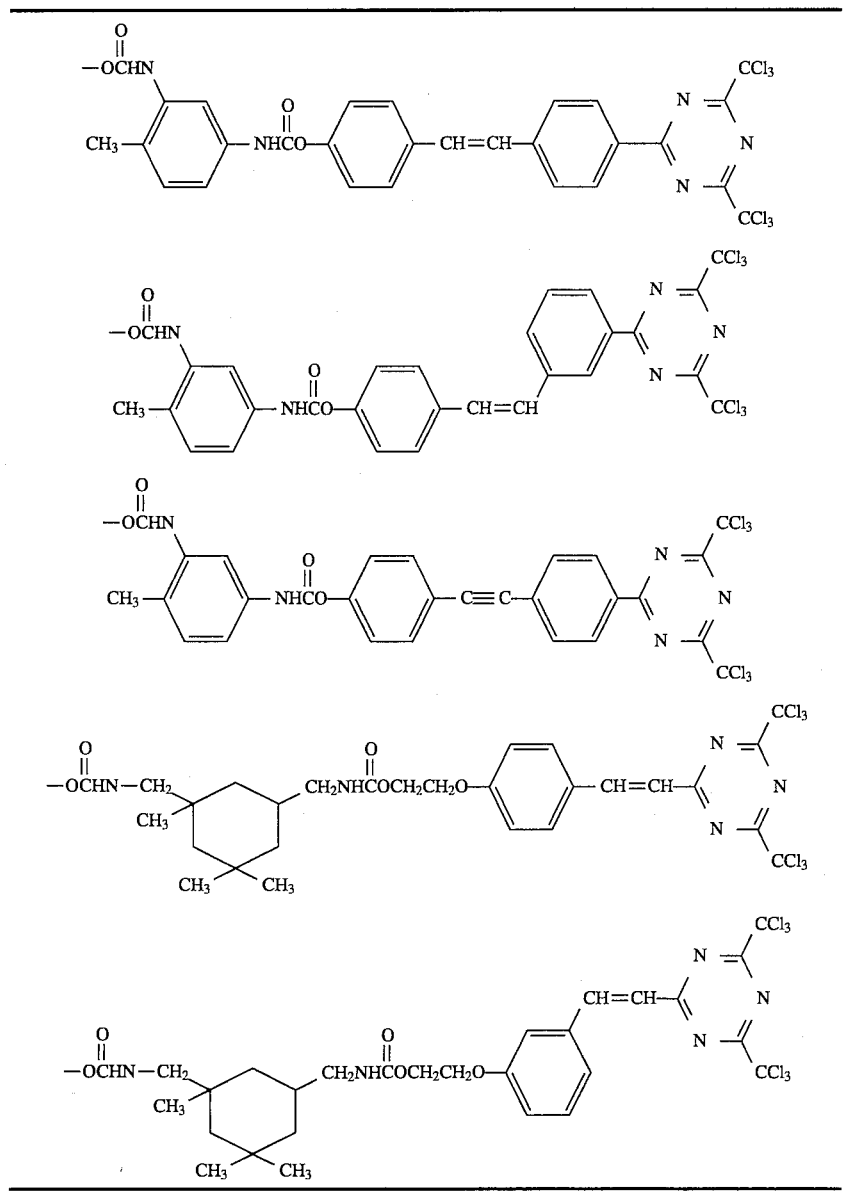

Examples of compounds having the formula $R^4(NCO)_y$ that are particularly useful in preparing the compounds of Formula II that are useful in this invention include aromatic isocyanates, such as, for example, tolylene-2,4-diisocyanate, tolylene-2,6-diisocyanate, 1,3-phenylene diisocyanate, 1,4-phenylene diisocyanate; aliphatic isocyanates, such as, for example, isophorone diisocyanate, 1,6-diisocyanatohexane; araliphatic isocyanates, such as, for example, 1,1'-methylenebis(4-isocyanatobenzene), 1,1',1''-methylidynetris(4-isocyanatobenzene); polymeric isocyanates, such as, for example, polymethylene poly(phenylisocyanate). Other species of these isocyanato-substituted compounds are listed in *Encyclopedia of Polymer Science and Engineering*, John Wiley & Sons, (New York, 1987), Vol 8, pp. 450–452. Compounds of Formula II derived from the isocyanato compound having the formula $R^4(NCO)_y$, where y represents an integer from 2 to 4, have never before been disclosed.

Representative examples of the moiety $R^4$ of the compounds of Formula II are listed in Table 3.

TABLE 3

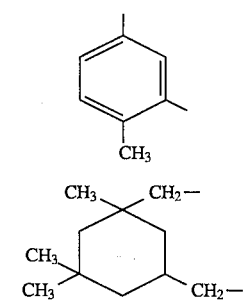

TABLE 3-continued

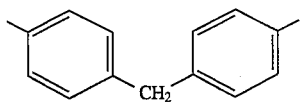

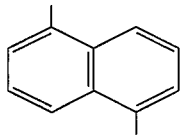

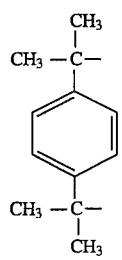

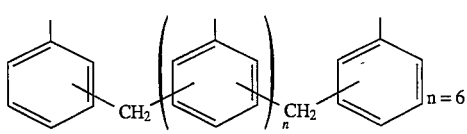

Representative examples of the moiety —NHCOO—$R^1$ of the compounds of Formula II are listed in Table 4.

TABLE 4

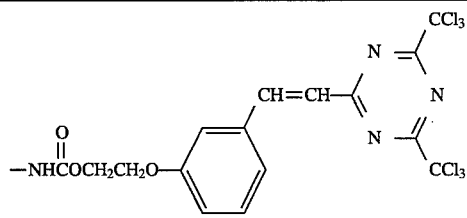

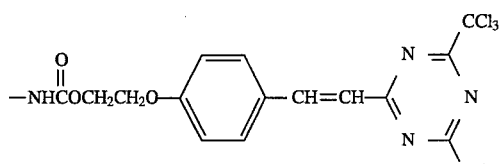

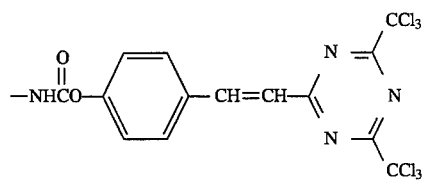

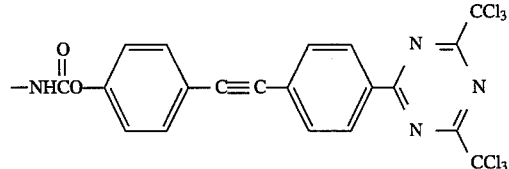

TABLE 4-continued

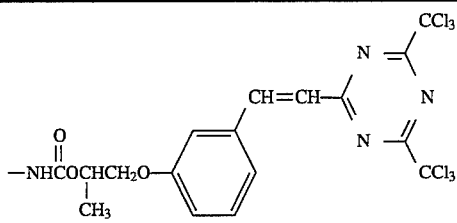

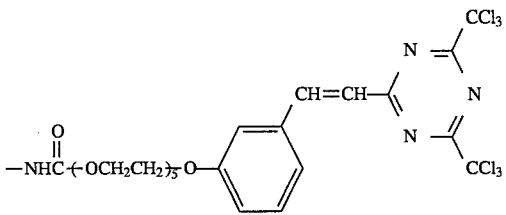

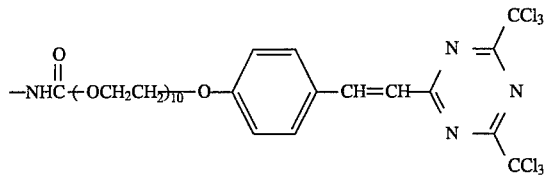

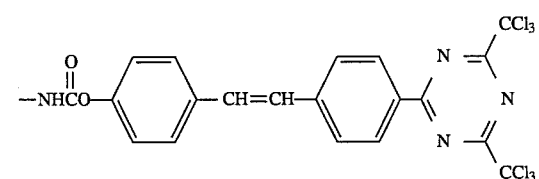

Examples of carboxylic acids having the formula $R^5(CO_2H)_w$ that are particularly useful in the preparation of the compounds of Formula III that are useful in this invention include alkylene dicarboxylic acids, such as succinic acid, maleic acid, suberic acid, 1,4-cyclohexanedicarboxylic acid; arylene carboxylic acids, such as terephthalic acid, 1,3,5-benzenetricarboxylic acid; compounds having the carboxylic acid groups linked by combinations of aryl and alkyl groups, such as 4-[4-(2-carboxybenzoyl)phenyl]butyric acid, 4-carboxyphenoxyacetic acid; compounds having cyclic anhydride groups, such as phthalic anhydride, maleic anhydride, trimellitic anhydride chloride, 1,2,4,5-benzenetetracarboxylic dianhydride, bicyclo(2.2.2)oct-7ene-2,3,5,6-tetracarboxylic dianhydride, 3,3',4,4'-benzophenone tetracarboxylic dianhydride; and maleic anhydride copolymers, such as copolymers of styrene and maleic anhydride, copolymers of an alkyl vinyl ether and maleic anhydride, and copolymers of butadiene and maleic anhydride.

Representative examples of the moiety $R^5$ of the compounds of Formula III are listed in Table 5.

TABLE 5

—$CH_2CH_2$—

—$CH_2CH_2CH_2CH_2CH_2CH_2$—

—CH=CH—

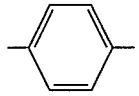

TABLE 5-continued

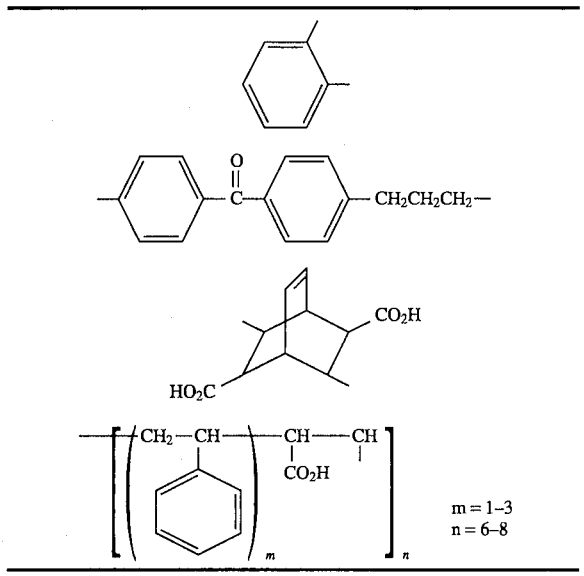

Representative examples of the moiety —COO—$R^1$ of the compounds of Formula III are listed in Table 6.

TABLE 6

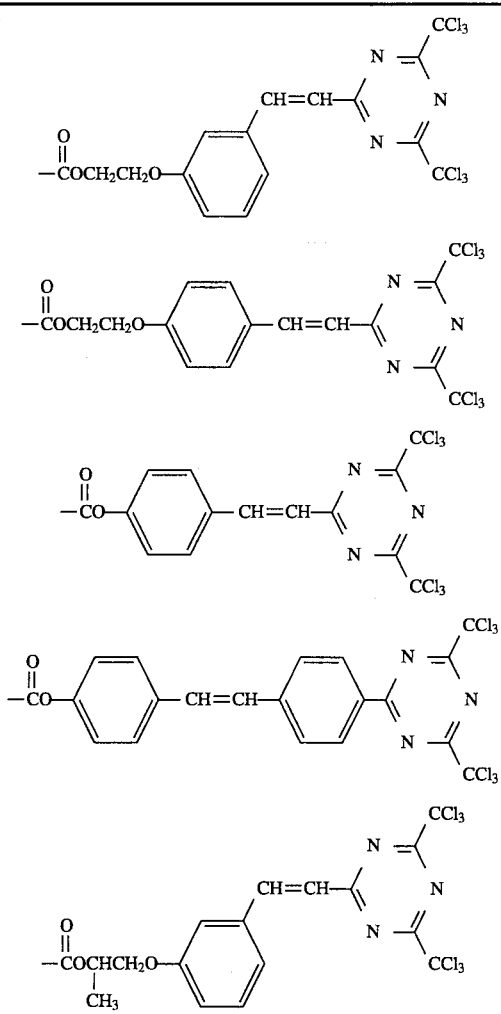

TABLE 6-continued

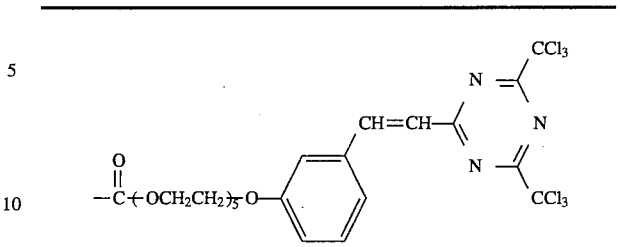

A particularly useful, and versatile, method for the preparation of the photoinitiators of Formula I involves the reaction of a hydroxyl-substituted halomethyl-1,3,5-triazine compound $R^1$—OH with the more reactive isocyanate group of the diisocyanate compound $R^2(NCO)_2$ to form the 1:1 adduct of Formula IX.

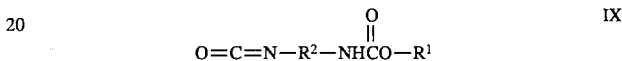

Depending on the reaction conditions, the 1:1 adducts of chromophore-substituted halomethyl-1,3,5-triazine compounds and diisocyanate compounds, such as tolylene-2,4-diisocyanate and isophorone diisocyanate, can be prepared and isolated at a purity level greater than 95%. This level of purity can be achieved by the dropwise addition of a hydroxyl-substituted halomethyl-1,3,5-triazine compound to an excess of the diisocyanate in the presence of a catalyst, such as dibutyltin dilaurate, at a temperature of from 15° to 30° C. Reaction solvents suitable for this reaction include, but are not limited to, toluene, 1,2-dichloroethane, tetrahydrofuran, and 2-butanone. The 1:1 adduct can be isolated from the reaction mixture by precipitation with another solvent and filtration of the precipitate. A benefit of this method is that the compound of Formula IX represents a very versatile intermediate. The isocyanato group (NCO) of the compound of Formula IX is capable of reacting with a wide variety of compounds having an active hydrogen atom, such as, for example $R^3(OH)_x$, under sufficiently mild conditions (e.g., 40° to 60° C.) so that the halomethyl group can be retained. It is possible, therefore, to systematically prepare a wide variety of chromophore-substituted halomethyl-1,3,5-triazine compounds in essentially quantitative yield. Because many of the polyoxyethylene derivatives are viscous syrups that would be difficult to purify, a quantitative yield is very desirable. Therefore, it is only necessary to remove the reaction solvent to isolate the product, or in many instances, the triazine compound may be allowed to remain in the reaction solvent until needed for preparing the light-sensitive articles of this invention.

Although the foregoing method is preferred, it is also possible to first react the hydroxyl-substituted compound $R^3(OH)_x$ with the diisocyanate. The resulting adduct can then be reacted with the triazine compound $R^1$—OH. The orientation of $R^1$ and $R^3$ will then be opposite, i.e., will occupy the position of $R^3$ and $R^3$ will occupy the position of $R^1$, but this change in orientation will have no significant effect with respect to the aspects of the compound relating to resistance to migration.

The photoinitiators of Formula II of this invention can be prepared by the reaction of a hydroxyl-substituted halomethyl-1,3,5-triazine compound $R^1$—OH with a multifunctional isocyanato-substituted compound under reaction conditions similar to those described for the preparation of the compound of Formula I. Species of a hydroxyl-substituted halomethyl-1,3,5-triazine compound $R^1$—OH different from the first species may be reacted with the isocyanato intermediate of Formula IX, thereby incorporating two different triazine groups in the photoinitiator. The photoinitiators of Formula II can be prepared in high yields, and they normally do not require further purification for use in light-sensitive compositions.

Whenever the compound of Formula I and the compound of Formula II can be derived from the same diisocyanate, a very simple, economical, two-step, one batch process can be employed to prepare mixtures of these compounds. For example, 2,4-bis(trichloromethyl)-6-[3-(2-hydroxyethoxy-)styryl]-1,3,5-triazine, hereinafter referred to as meta-MOSTOL (1.1 mole), and tolylene-2,4-diisocyanate, hereinafter referred to as TDI (1.0 mole), can be reacted at room temperature. To the reaction mixture can be added a polyoxyethylene nonylphenol having a mole ratio of 5 ("IGEPAL CO-520", obtained from Rhone-Poulenc) (0.9 mole), hereinafter referred to as POENP5, and the temperature raised to 60° C. to produce a mixture containing approximately 80% meta-MOSTOL/TDI/POENP5 (compound of Formula I), 15% [meta-MOSTOL]$_2$/TDI (compound of Formula II), and 5% of the 2:1 adduct POENP5/TDI. This mixture can be used directly in a light-sensitive composition without further purification.

The photoinitiators of Formula III can be prepared by the reaction of a hydroxyl-substituted halomethyl-1,3,5-triazine compound $R^1$—OH with an acid $R^5(CO_2H)_w$ or other activated carboxylic acid derivative of $R^5(CO_2H)_w$, such as an acid chloride or acid anhydride. A particularly useful method is the mild one-pot esterification method described in A. Hassner and V. Alexanian, *Tetrahedron Letters*, No. 46, pp. 4475–4478, 1978 (Pergamon Press Ltd., United Kingdom). According to this procedure, the hydroxyl-substituted halomethyl-1,3,5-triazine compound $R^1$—OH is reacted with the carboxylic acid $R^5(CO_2H)_w$ in a solvent in the presence of dicyclohexylcarbodiimide and a catalyst, such as 4-pyrrolidinopyridine, at room temperature, to give good yields of the photoinitiators of Formula III. According to this same procedure, two equivalents of the halomethyl-1,3,5-triazine compound $R^1$—OH can be reacted with a cyclic anhydride derivative of $R^5(CO_2H)_w$ to esterify both carboxyl groups of each anhydride group. The mild conditions are preferred because undesirable side reactions, which can decompose the halomethyl group, are minimized. Compounds of Formula III can also be prepared from cyclic anhydride derivatives of $R^5(CO_2H)_w$ having at least two cyclic anhydride groups. Each anhydride group is reacted with one equivalent of the compound $R^1$—OH to form the half-ester of each anhydride. The reaction conditions involve either the heating of the reactants with an acid catalyst in a solvent such as toluene or xylene at temperatures in the range of 100°–140° C. or melting the reactants together. These methods are less preferred because of undesirable side reactions, which can decompose the halomethyl group. Another useful and versatile method is to react compound $R^1$—OH with the carboxylic acid chloride $R^5(COCl)_w$ in the presence of an amine compound, such as triethyl amine, This reaction is normally conducted at room temperature and is sufficiently mild to preserve the halomethyl groups.

It is preferred to limit the molecular weight of the compounds of Formulae I, II, and III in order that an effective amount of the light-sensitive portion of the photoinitiator can be delivered by a relatively low amount of the total photoinitiator. As used herein, "an effective amount" means an amount sufficient to initiate polymerization of the polymerizable ethylenically unsaturated compound. Generally, the amount of the compound of Formulae I, II, or III can range from about 1 to about 25% by weight of the layer of photopolymerizable material, more preferably ranging from about 1 to about 15% by weight of the layer of photopolymerizable material. The preferred molecular weight of the compounds of Formulae I, II, or III can range from approximately 5,000 or less per each chromophore-substituted triazine unit, more preferably 2,000 or less per each chromophore-substituted triazine unit. The preferred molecular weight of the compound of Formula I is preferably greater than about 600 per each chromophore-substituted triazine unit. The preferred molecular weight of the compound of Formula II is preferably greater than about 500 per each chromophore-substituted triazine unit. The preferred molecular weight of the compound of Formula III is preferably greater than about 500 per each chromophore-substituted triazine unit. The percentage by weight of the chromophore-substituted halomethyl-1,3,5-triazine moiety in the photoinitiators of this invention is preferably greater than about 8%, based on the total weight of the photoinitiator.

The polymerizable compounds having at least one ethylenically unsaturated group suitable for use in the layer of photopolymerizable material of the article of the present invention are those having at least one ethylenically unsaturated double bond in their chemical structures. They can be in the form of monomers, prepolymers, i.e., dimers, trimers and other oligomers as well as mixtures and copolymers thereof. Examples of these compounds include esters of unsaturated carboxylic acids and aliphatic polyols; and amides of unsaturated carboxylic acids and aliphatic polyamines.

Examples of such unsaturated carboxylic acids are acrylic acid, methacrylic acid, itaconic acid, crotonic acid, isocrotonic acid, and maleic acid.

Examples of the esters of aliphatic polyols and unsaturated carboxylic acids are acrylates, such as ethylene glycol diacrylate, triethylene glycol diacrylate, 1,3-butanediol diacrylate, tetramethylene glycol diacrylate, propylene glycol diacrylate, trimethylolpropane triacrylate, trimethylolethane triacrylate, 1,4-cyclohexanediol diacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol hexaacrylate, sorbitol triacrylate, sorbitol tetraacrylate, sorbitol pentaacrylate, sorbitol hexaacrylate; methacrylates such as tetramethylene glycol dimethacrylate, triethylene glycol dimethacrylate, trimethylolpropane trimethacrylate, trimethylolethane trimethacrylate, ethylene glycol dimethacrylate, 1,3-butanediol dimethacrylate, pentaerythritol dimethyacrylate, pentaerythritol trimethacrylate, dipentaerythritol dimethacrylate, sorbitol trimethacrylate, sorbitol tetramethacrylate, bis(p-(3-methacryloxy-2-hydroxypropoxy)phenyl)dimethylmethane, bis-(p-methacryloxyethoxy)phenyl)dimethylmethane; itaconates such as ethylene glycol diitaconate, propylene glycol diitaconate, 1,3-butanediol diitaconate, 1,4-butanediol diitaconate, tetramethylene glycol diitaconate, pentaerythritol diitaconate, and sorbitol tetraitaconate; crotonates such as ethylene glycol dicrotonate, tetramethylene glycol dicrotonate, pentaerythritol dicrotonate, and sorbitol tetracrotonate; isocrotonates such as ethylene glycol diisocrotonate, pentaerythritol diisocrotonate, and sorbitol tetraisocrotonate; maleates such as ethylene glycol dimaleate, triethylene glycol dimaleate, pentaerythritol dimaleate, and sorbitol-tetramaleate; and mixture of the foregoing esters.

Examples of the amides of aliphatic polyamine compounds and unsaturated carboxylic acids include methylenebis-acrylamide, methylene-bis-methacrylamide, 1,6-hexamethylene-bis-acrylamide, 1,6-hexamethylene-bismethacrylamide, diethylenetriamine-tris-acrylamide, xylylene-bis-acrylamide, and xylylene-bis-methacrylamide.

Examples of oligomers and prepolymers having ethylenically unsaturated groups include acrylated epoxy oligomers, acrylated aliphatic urethane oligomers, acrylated aromatic urethane oligomers, acrylated polyester oligomers, and acrylated acrylic oligomers. Many of these types of materials are commercially available. Other useful examples include the acrylated urethane oligomers described in U.S. Pat. No. 4,304,923, and the methacrylated and acrylated sulfocompound oligomers described in U.S. Pat. No. 4,855,384.

An optional binder or combination of binders for the layer of photopolymerizable material can be selected from among linear, solvent soluble organic polymers. The actual polymer to be selected depends upon several factors, such as compatibility with other components of the layer of photopolymerizable material, solubility in coating solvent, concentration, molecular weight, etc. Examples of polymers soluble in organic solvents that are useful as binders include such polymers as polyvinyl butyral, polyvinyl formal, polystyrene, polyvinyl chloride, polyvinylidene chloride, polyacrylic esters, polyvinyl acetates, polyesters, polyurethanes and polyamides, polyethylenes, phenoxy.resins, copolymers of vinyl acetate and vinyl chloride, copolymers of styrene and isoprene, copolymers of styrene and butadiene, copolymers of styrene and acrylonitrile; terpolymers of vinyl acetate, methyl methacrylate, and butyl methacrylate, terpolymers of N-hydroxymethyl acrylamide, butyl acrylate, and methyl methacrylate. Whenever it is desirable to process the layer of photopolymerizable material in water or weakly aqueous alkaline solutions, polymers that will assist the solubility or dispersibility in water or weakly aqueous alkaline solutions are preferred. The solubility or dispersibility of the polymer is a function of the chemical nature of either the substituents or segments within the polymer. Polymers having ionic substituents such as alkyl and aryl carboxylic acid groups, sulfonic acid groups, phosphonic acid groups, phenolic groups, and their salts, as well as aryl and alkyl amine groups, such as pyridine group and piperidine group, and quaternary salts of alkyl and aryl amine groups are particularly useful in promoting solubility or dispersibility in water. Preferred binders are selected from addition polymers having carboxyl groups in the side chain. These binders include copolymers of acrylic acid, copolymers of methacrylic acid, copolymers of itaconic acid, copolymers of crotonic acid, copolymers of maleic acid, copolymers of partially esterified maleic acid, and hydroxy-containing copolymers that have been reacted with succinic anhydride as described in assignee's copending application, U.S. Ser. No. 07/716,317, filed Jun. 17, 1991. Particularly preferred are copolymers of alkyl methacrylate esters (wherein the alkyl group is methyl, ethyl, propyl, butyl, 2-hydroxyethyl) and methacrylic acid or acrylic acid, copolymers of alkyl acrylate esters and methacrylic acid or acrylic acid, copolymers of styrene and acrylic acid, copolymers of styrene and methacrylic acid, copolymers of styrene and maleic anhydride and their half-ester derivatives, copolymers of alkyl vinyl ethers and maleic anhydride and their half-ester derivatives, copolymers of polyvinyl acetate and crotonic acid, and copolymers of polyvinyl formal and polyvinyl butyral that have been reacted with succinic anhydride as described in assignee's copending application, U.S. Ser. No. 07/716,317, filed Jun. 17, 1991. Polymers or copolymers that contain segments that are useful for promoting solubility or dispersibility in water can be derived from water soluble monomers, such as, for example, ethylene oxide, vinyl pyrrolidone, vinyl alcohol, and acrylamide. Examples of these polymers include polyvinyl alcohol, polyvinyl pyrrolidone, polyethylene oxide, polyethylene glycol, and polycaprolactone.

The layer of photopolymerizable material may contain colorants such as pigments and dyes. Any dye that is soluble in the coating solvent and does not adversely affect the light sensitivity of the layer of photopolymerizable material, inhibit the polymerization reaction, or migrate excessively into adjacent layers, is suitable. Pigments can be selected from the many types that are commercially available for matching color specifications established by the color printing industry. Pigments are more preferred as colorants in photopolymerizable compositions, and, more particularly, in photopolymerizable compositions used in color proofing applications. Pigments are preferred because they have a lower tendency than dyes to migrate between layers. The pigment or combinations of pigments can be dispersed by milling the pigment in the photopolymerizable composition. More preferably, the pigment is dfspersed by milling the pigment in a dispersing resin or combination of resins and then added to the photopolymerizable composition. The particular type of dispersion resin and the pigment-to-resin ratio chosen will depend on the particular pigment, surface treatment of the pigment, dispersing solvent, milling process, and the quality of dispersion required.

The layer of resin contiguous to the photosensitive layer can be any thermoplastic resin. Examples of thermoplastic resins suitable for the layer of resin include thermoplastic linear polymers, such as, for example, polyvinyl butyral, polyvinyl formal, polystyrene, polyvinyl chloride, polyvinylidene chloride, polyacrylic esters, polyvinyl acetates, polyesters, polyurethanes and polyamides, polyethylenes, phenoxy resins, copolymers of vinyl acetate and vinyl chloride, copolymers of styrene and isoprene, copolymers of styrene and butadiene, copolymers of styrene and acrylonitrile; terpolymers of vinyl acetate, methyl methacrylate, and butyl methacrylate, terpolymers of N-hydroxymethyl acrylamide, butyl acrylate, and methyl methacrylate. The layer of resin may comprise one or more resins, and may optionally include other additives, such as surfactants, plasticizers, pigments, optical brighteners, coalescence aids, etc.

The layer of photopolymerizable material and the layer of resin may be placed in contact by any of several methods. In one method, one layer can be solution coated onto the other. It is preferred to use a coating solvent that will minimize degradation of the layer upon which the coating solution is being deposited. Another method is to laminate the two layers together by means of heat and pressure.

The article of this invention is especially valuable in preparing multilayer, light-sensitive articles that can be used to produce four-color proofs. Such articles, which are composites, are described in U.S. Pat. Nos. 3,671,236 and 4,596,757, incorporated herein by reference. The article, which can be prepared in the form of a sheet, comprises, in order, a carrier support, a release layer overlying the support, a layer of photopolymerizable material overlying the release layer, and a layer of thermoplastic resin overlying the layer of photopolymerizable material. In one process, the photosensitive article is laminated to a receptor sheet via the layer of resin by first transferring the layer of resin, layer of photopolymerizable material, and release layer to one side of a receptor sheet, the layer of resin being in contact with the receptor sheet. The carrier support is then peeled away, usually manually. The layer of photopolymerizable material is then imagewise exposed to actinic radiation. The release layer and the unexposed areas of the colored layer of photopolymerizable material are then dissolved away with a developer solution, thus leaving a colored image disposed on the receptor sheet. Each of these steps is then repeated a least once for a different color, whereby the colored image of the next photosensitive article is applied over the previous colored image on the same side of the receptor sheet. In the usual case, four sheets are employed to produce a four-color proof. The colors consist of cyan, magenta, yellow, and black. The photoinitiators that are useful in this invention overcome the problem of excessive migration of the photoinitiator from the layer of photopolymerizable material to the layer of resin of the composite. This migration would be expected to occur during the coating or laminating steps previously described or during storage of the article, or during the lamination process used to superimpose the sheets of different colors. The problem of migration of the photoinitiator manifests itself as a discoloration of the background of the surprint proof. The discoloration results from the presence of the chromophore of a photoinitiator that has migrated from the layer of photopolymerizable material, a colored photodecomposition product, or both. The extent of discoloration is cumulative, i.e., the more sheets that are used to make the proof, the more discolored is the background. In an ideal situation, even after application of multiple sheets to the receptor sheet, the background areas of the image should match the original color of the receptor sheet.

In addition to the foregoing, it has been discovered that some of the compounds of this invention, especially those derived from polyoxyalkylene surfactants, enhanced the solvent developability of the layer of photopolymerizable material.

PREPARATIONS

The following preparatory examples illustrate methods for synthesizing photopolymerization initiators (photoinitiators) that are useful in this invention. All percentages are percentages by weight, unless indicated otherwise.

Preparation I

This preparation illustrates the synthesis of 2,4-bis-(trichloromethyl)-6-[4-(2-hydroxyethoxy)styryl]-1,3,5-triazine, hereinafter referred to as para-MOSTOL.

A stirred solution of 2,4-bis(trichloromethyl)-6-methyl-1,3,5-triazine (90 g, 0.27 mole), 4-(2-hydroxyethoxy)benzaldehyde (50 g, 0.30 mole), and ammonium acetate (12 g) in 220 mL of methanol was refluxed for 7 hours. After the mixture was allowed to cool, the product that crystallized from the reaction solution was filtered, washed with cold methanol, and dried to yield 100 g of para-MOSTOL, mp 173°–177° C. The product was further purified by recrystallization in toluene. The structural formula of para-MOSTOL is shown below.

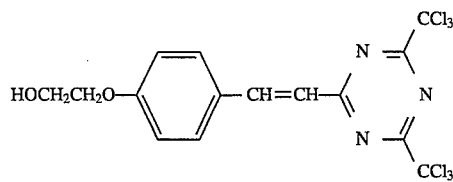

Preparation II

This preparation illustrates the reaction of 2,4-bis(trichloromethyl)-6-[4-(2-hydroxyethoxy)styryl]-1,3,5-triazine (para-MOSTOL) with 2,4-tolylene diisocyanate to prepare a derivative that will hereinafter be referred to as para-MOSTOL/TDI. The purity of the derivative exceeded 95%.

A solution was prepared by dissolving 2,4-bis(trichloromethyl)-6-[4-(2-hydroxyethoxy)styryl]-1,3,5-triazine (47.8 g, 0.10 mole) in 300 mL of toluene at a temperature of 45° C. This solution was added dropwise to a stirred solution of 2,4-tolylene diisocyanate (52.2 g, 0.30 mole) in 200 mL of 1,2-dichloroethane over a period of 3 hours at a temperature of 23° C. Analysis by gel permeation chromatography (GPC) indicated that the reaction was complete after an additional 2 hours, and the reaction products were approximately 95% of the 1:1 adduct para-MOSTOL/TDI and 5% of the 2:1 adduct [para-MOSTOL]$_2$/TDI. The reaction mixture was concentrated to about 50% of the original volume by means of a under vacuum by means of a rotary evaporator and poured into 1,000 mL of hexane with vigorous stirring to produce a slightly yellow precipitate. This precipitate was collected by filtration, dispersed in 300 mL of hexane, refiltered, and dried in a vacuum desiccator to yield 60.0 g of a slightly tan solid, mp 75°–79° C. Analysis by GPC showed the product to be 96% of the 1:1 adduct having the structural formula shown below and 4% of the 2:1 adduct (See Preparation IX).

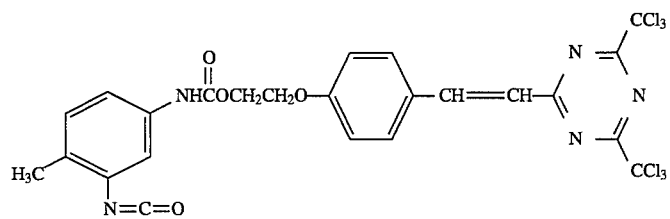

Preparation III

This preparation illustrates the reaction of para-MOSTOL/TDI (Preparation II) with a polyoxyethylene nonylphenol having a mole ratio of 5 (hereinafter POENP5), to prepare a chromophore-substituted triazine compound that will hereinafter be referred to as para-MOSTOL/TDI/POENP5.

A commercially available sample of polyoxyethylene nonylphenol ("IGEPAL CO-520" obtained from Rhone-Poulenc), contained approximately 5% water present as an impurity. This water was removed by a vacuum azeotropic distillation of a solution containing polyoxyethylene nonylphenol (1.0 kg) in 1.0 L of toluene until the concentration of polyoxyethylene nonylphenol in the solution was approximately 70–80%. Analysis by the Karl Fischer method indicated water to be present at a concentration of less than 100 ppm. The final concentration of polyoxyethylene nonylphenol was determined to be 79.2%. The structure of polyoxyethylene nonylphenol compounds useful in this invention usually only indicates the mole ratio of ethylene oxide to nonylphenol used in their preparation. For polyoxyethylene nonylphenol having the trademark "IGEPAL CO-520", this mole ratio is 5. Analysis by mass spectrometry and nuclear magnetic resonance (nmr), however, showed that the polyoxyethylene nonylphenol having the trademark "IGEPAL CO-520" to contain a mixture of the structural formulae shown below.

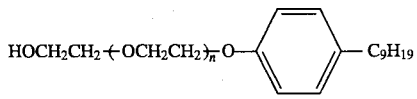

n=2 to 8.

To a dispersion of para-MOSTOL/TDI (13.04 g, 0.02 mole) in 70 mL of toluene was added the dry, 79.2% solution of polyoxyethylene nonylphenol (11.34 g, 0.02 mole, mole ratio=5) in toluene followed by dibutyltin dilaurate (0.030 g). The reaction mixture was heated for 3 hours at a temperature of 60° C. GPC and infrared analysis indicated that the reaction was complete. A clear yellow-brown viscous syrup was isolated by removal of the toluene solvent under vacuum by means of a rotary evaporator. The product para-MOSTOL/TDI/POENP5 has the structural formula shown below.

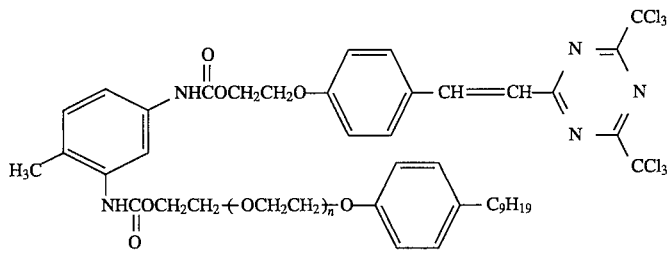

where n=4.

Preparation IV

This preparation illustrates the reaction of 2,4-bis(trichloromethyl)-6-[4-(2-hydroxyethoxy)styryl]-1,3,5-triazine (para-MOSTOL) with tolylene-2,4-diisocyanate to prepare a mixture of para-MOSTOL/TDI and [para-MOSTOL]$_2$/TDI.

A dispersion containing 2,4-bis(trichloromethyl)-6-[p-(2-hydroxyethoxy)styryl]-1,3,5-triazine (36.65 g, 0.077 mole), tolylene-2,4-diisocyanate (13.34 g, 0.077 mole), and dibutyltin dilaurate (0.050 g) in 200 mL of 1,2-dichloroethane was stirred for 48 hours at a temperature of 23° C. The paste that formed was filtered and dried in a vacuum desiccator to provide approximately 37 g of a slightly yellow solid. GPC analysis indicated that the product was a mixture containing about 80% of the 1:1 adduct para-MOSTOL/TDI and 20% of the 2:1 adduct [para-MOSTOL]$_2$/TDI.

Preparations V–VIII

These preparations describe the reaction product of the mixture of Preparation IV with a series of alkylated polyoxyethylene nonylphenol surfactants of increasing molecular weights.

Preparation V

A solution containing the product from Preparation IV (5.0 g, 0.0077 mole), a polyoxyethylene nonylphenol ("IGEPAL CO-210" obtained from Aldrich Chemical Co. Inc., molecular weight 352, 2.70 g, 0.0077 mole, mole ratio=2, hereinafter POENP2), and 1 drop of dibutyltin dilaurate in 30 mL of 1,2-dichloroethane was heated at a temperature of 60° C. for 3 hours. Infrared analysis showed that the reaction was complete. The solution was concentrated under vacuum by means of a rotary evaporator to give a viscous syrup. The primary product, para-MOSTOL/TDI/POENP2, has the structural formula shown in Preparation III, with the exception that n=1.

Preparations VI–VIII

The procedure of Preparation V was repeated except that the polyoxyethylene nonylphenols shown below were substituted for the polyoxyethylene nonylphenol having the trademark "IGEPAL CO-210".

| Preparation | Trademark of polyoxyethylene nonylphenol | Amount of polyoxyethylene nonylphenol (g) | Mole ratio of polyoxyethylene nonylphenol (n + 1) |
|---|---|---|---|
| VI | "IGEPAL CO-720" | 6.5 | 12 |
| VII | "IGEPAL CO-890" | 17.9 | 40 |
| VIII | "IGEPAL CO-990" | 41.0 | 100 |

Preparation IX

This preparation illustrates the reaction of 2,4-bis(trichloromethyl)-6-[3-(2-hydroxyethoxy)styryl]-1,3,5-triazine (para-MOSTOL) with 2,4-tolylene diisocyanate to prepare the chromophore-substituted triazine compound referred to hereinafter as [para-MOSTOL]$_2$/TDI.

A solution containing para-MOSTOL, (9.56 g, 0.02 mole), tolylene-2,4-diisocyanate (1.74 g, 0.01 mole), and dibutyltin dilaurate (0.025 g) in 100 mL of 1,2-dichloroethane was heated at a temperature of 60° C. for 4 hours. Infrared analysis indicated that the reaction was complete. The solvent was removed under vacuum by means of a rotary evaporator and the product, [para-MOSTOL]$_2$/TDI, was isolated as a light yellow solid and has the structural formula shown below.

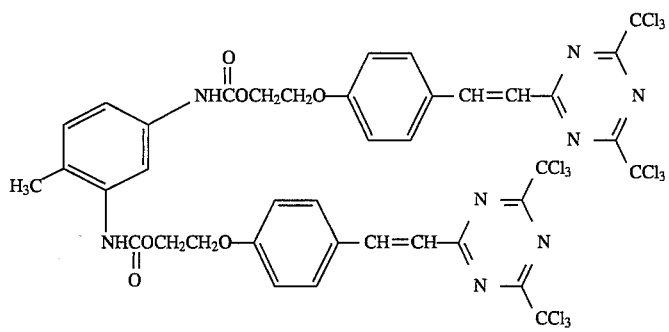

Preparation X

This preparation illustrates the synthesis of 2,4-bis-(trichloromethyl)-6-[3-(2-hydroxyethoxy)styryl]-1,3,5-triazine, referred to hereinafter as meta-MOSTOL.

A stirred solution of 2,4-bis(trichloromethyl)-6-methyl-1,3,5-triazine (103 g, 0.31 mole), 3-(2-hydroxyethoxy)benzaldehyde (47 g, 0.28 mole), and ammonium acetate (10.5 g) in 270 mL of methanol was refluxed for 12 hours. After the mixture had cooled, an additional 80 mL of methanol was added, followed by 112 mL of water. The product precipitated from the reaction solution, was filtered and dried to yield 74 g of meta-MOSTOL, mp 127°–128° C., which has the structural formula shown below.

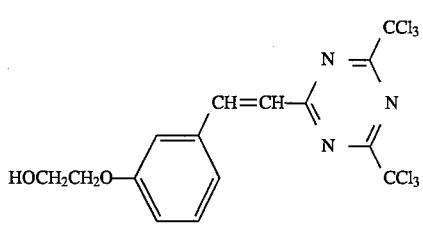

Preparation XI

This preparation illustrates the reaction of 2,4-bis(trichloromethyl)-6-[3-(2-hydroxyethoxy)styryl]-1,3,5-triazine with 2,4-tolylene diisocyanate to prepare the derivative referred to hereinafter as meta-MOSTOL/TDI. The purity exceeded 95%.

A solution was prepared by dissolving 2,4-bis(trichloromethyl)-6-[3-(2-hydroxyethoxy)styryl]-1,3,5-triazine (47.8 g, 0.10 mole) in 300 mL of toluene at a temperature of 45° C. This solution was added dropwise to a stirred solution of 2,4-tolylene diisocyanate (52.2 g, 0.30 mole) in 200 mL of toluene over a period of 3 hours at a temperature of 23° C. Analysis by GPC indicated that the reaction was complete after an additional 2 hours and the reaction products were approximately 95% of the 1:1 adduct meta-MOSTOL/TDI and 5% of the 2:1 adduct [meta-MOSTOL]$_2$/TDI. The reaction mixture was poured into 1,000 mL of hexane with vigorous stirring to produce a white precipitate. This precipitate was collected by filtration, dispersed again in 300 mL of hexane, refiltered, and dried in a vacuum desiccator to yield 59.0 g of a slightly tan solid, mp 85°–89° C. Analysis by GPC showed the product to contain approximately 95% of the 1:1 adduct and 5% of the 2:1 adduct. The structure of the 1:1 adduct meta-MOSTOL/TDI has the structural formula shown below.

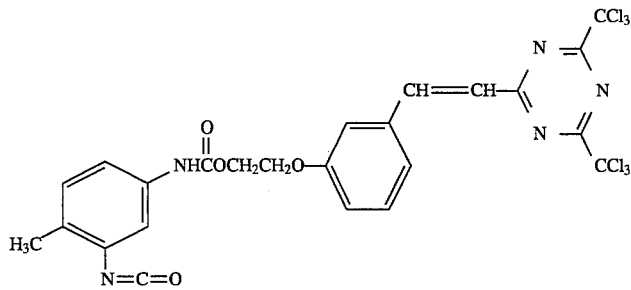

Preparation XII

This preparation illustrates the reaction of meta-MOSTOL/TDI (Preparation XI) with a polyoxyethylene nonylphenol ("IGEPAL CO-520") to prepare the chromophore-substituted triazine compound referred to hereinafter as meta-MOSTOL/TDI/POENP5.

The procedure of Preparation III was repeated, with the exceptions that meta-MOSTOL was substituted for para-MOSTOL and a 66% dried solution of polyoxyethylene nonylphenol was used in place of the 79.2% solution. The product, meta-MOSTOL/TDI/POENP5, was isolated as a clear, pale yellow syrup and has the structural formula shown below.

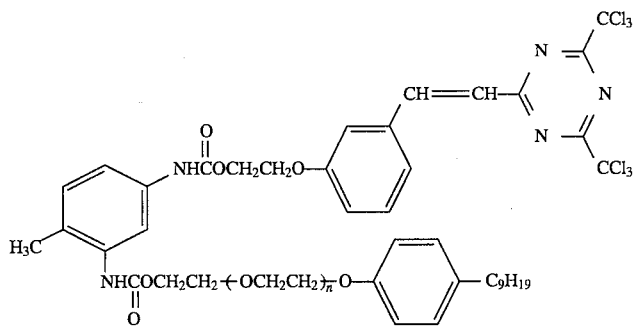

where n=4.

Preparation XIII

This preparation illustrates the reaction of 2,4-bis(trichloromethyl)-6-[3-(2-hydroxyethoxy)styryl]-1,3,5-triazine (meta-MOSTOL) with tolylene-2,4-diisocyanate to prepare a mixture containing approximately 80% of the 1:1 adduct meta-MOSTOL/TDI and 20% of the 2:1 adduct [meta-MOSTOL]$_2$/TDI.

The procedure used in Preparation IV was repeated with the exception that meta-MOSTOL was substituted for para-MOSTOL. A white solid was isolated which was shown by infrared analysis to be primarily the 1:1 adduct meta-MOSTOL/TDI having the general structure shown in Preparation XI. GPC analysis indicated that the product was a mixture containing about 80% meta-MOSTOL/TDI and 20% [meta-MOSTOL]$_2$/TDI (Preparation XVIII).

Preparations XIV–XV

These preparations illustrate the reaction of the product of Preparation XIII with polyoxyethylene nonylphenol compounds where the mole ratio=2 ("IGEPAL CO-210") and where the mole ratio=5 ("IGEPAL CO-520").

Preparation XIV

The procedure of Preparation V was repeated for Preparation XIV, with the exceptions that meta-MOSTOL/TDI and [meta-MOSTOL]$_2$/TDI were substituted for para-MOSTOL/TDI and [para-MOSTOL]$_2$/TDI, respectively, to give a clear viscous syrup, which was isolated and determined to be a mixture having as the primary product meta-MOSTOL/TDI/POENp2, and a smaller amount of [meta-MOSTOL]$_2$/TDI.

Preparation XV

The procedure of Preparation V was repeated for Preparation XV, with the exceptions that meta-MOSTOL/TDI and [meta-MOSTOL]$_2$/TDI were substituted for para-MOSTOL/TDI and [para-MOSTOL]$_2$/TDI, respectively, and that polyoxyethylene nonylphenol (3.46 g, 0.0077 mole, mole ratio=5) was substituted for the polyoxyethylene nonylphenol (mole ratio=2), to give a clear viscous syrup, which was isolated and determined to be a mixture having as the primary product meta-MOSTOL/TDI/POENP5, and a smaller amount of [meta-MOSTOL]$_2$/TDI.

Preparation XVI

This preparation illustrates a simple, two-step, one-batch reaction of 2,4-bis(trichloromethyl)-6-[3-(2-hydroxyethoxy)styryl]-1,3,5-triazine (meta-MOSTOL), 2,4-tolylene diisocyanate (TDI), and polyoxyethylene nonylphenol ("IGEPAL CO-520") to prepare a mixture containing 80% meta-MOSTOL/TDI/POENP5, 15% [meta-MOSTOL]$_2$/TDI, and 5% [POENP5]$_2$/TDI, which mixture can function as a photoinitiator.

To a stirred dispersion containing 2,4-bis(trichloromethyl)-6-[3-(2-hydroxyethoxy)styryl]-1,3,5-triazine (55.00 g, 0.1151 mole) and 2,4-tolylene diisocyanate (18.2 g, 0.102 mole) in 200 mL of toluene at a temperature of 16° C. was added dibutyltin dilaurate (0.150 g). A slight exotherm raised the temperature of the reaction mixture to 19° C. and the reaction mixture became clear after approximately 20 minutes. The meta-MOSTOL had completely reacted in 5 hours and the resulting mixture was analyzed by GPC and found to contain the following materials: meta-MOSTOL/TDI (54.5 g, 0.0837 mole), (meta-MOSTOL)$_2$/TDI (17.7 g, 0.0314 mole), and 2,4-tolylene diisocyanate (0.9 g, 0.0052 mole).

To this mixture was added a 79.2% solution of polyoxyethylene nonylphenol ("IGEPAL CO-520") (58.92 g, 0.0941 mole) in toluene and the solution was heated to a temperature of 60° C. and maintained at that temperature for 4 hours. Infrared analysis indicated that all of the isocyanate had reacted. The reaction mixture was determined by high performance liquid chromatography (HPLC) analysis to contain approximately 80% (96.0 g) metaMOSTOL/TDI/POENP5, 15% (17.8 g) [meta-MOSTOL]$_2$/TDI, and 5% (6.0 g)[POENP5]$_2$/TDI. Removal of the toluene under vacuum by means of a rotary evaporator provided a slightly brown viscous syrup. For ease of handling, this material was redissolved in sufficient methyl ethyl ketone to produce a solution having a concentration of approximately 50%.

Preparations XVII–XX

These preparations illustrate reactions of the compound of Preparation X, meta-MOSTOL, with a variety of isocyanato-substituted compounds.

Preparation XVII

This preparation illustrates the reaction of two moles of 2,4-bis(trichloromethyl)-6-[4-(2-hydroxyethoxy)styryl]-1,3,5-triazine (Preparation IX) with one mole of isophorone diisocyanate.

A solution containing 2,4-bis(trichloromethyl)-6-[4-(2-hydroxyethoxy)styryl]-1,3,5-triazine (4.78 g, 0.10 mole), isophorone diisocyanate (1.11 g, 0.005 mole), and dibutyltin dilaurate (0.025 g) in mL of 1,2-dichloroethane was refluxed for 8 hours. Infrared analysis indicated that the reaction was complete and the reaction product was consistent with formation of the diadduct. The solvent was removed under vacuum by means of a rotary evaporator and a glassy yellow solid having the structural formula of the dimer adduct shown below was isolated.

hereinafter as [meta-MOSTOL]$_3$/CYTH. A solution containing meta-MOSTOL (9.56 g, 0.02 mole), polyisocyanate (8.23 g) (available from American Cyanamid Co. under the trade name "CYTHANE 3160" and having an equivalent weight of 411), and dibutyltin dilaurate (0.06 g) in 60 mL of methyl ethyl ketone was heated at a temperature of 55° C. for 1 hour. Infrared analysis indicated that the reaction was

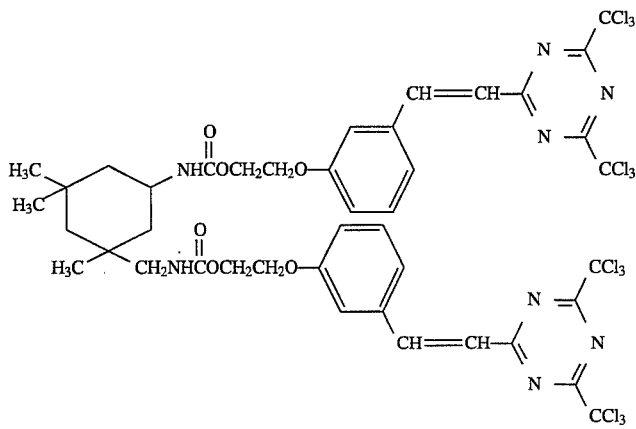

Preparation XVIII

This preparation illustrates the reaction of 2,4-bis(trichloromethyl)-6-[3-(2-hydroxyethoxy)styryl]-1,3,5-triazine with 2,4-tolylene diisocyanate to prepare the chromophore-substituted triazine compound referred to hereinafter as [meta-MOSTOL]$_2$/TDI.

The procedure of Preparation XVII was repeated, with the exception that tolylene-2,4-diisocyanate (0.87 g, 0.005 mole) was substituted for the isophorone diisoyanate. A tan solid, which was determined by infrared and nmr analysis to be consistent with the dimer adduct having the structural formula shown below was isolated.

completed, and the solvent was removed under vacuum by means of a rotary evaporator to give a light yellow solid. The structural formula of the product shown below, [meta-MOSTOL]$_3$/CYTH, is based on the structure of the "CYTHANE 3160" polyisocyanate starting material, based on product literature from the supplier.

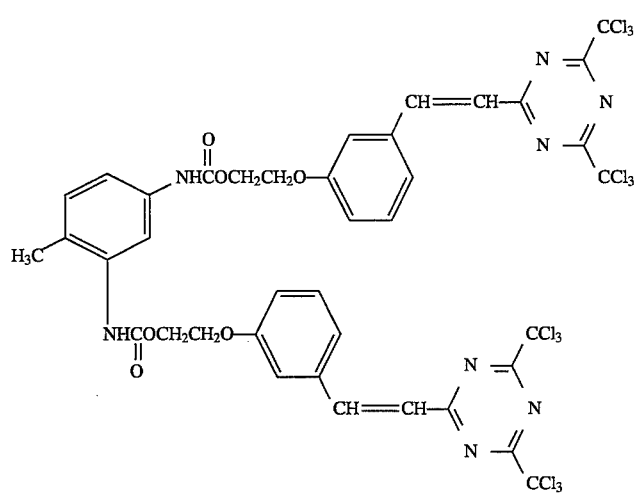

Preparation XIX

This preparation illustrates the reaction of meta-MOSTOL with a polyisocyanate ("CYTHANE 3160") to prepare the chromophore-substituted triazine compound referred to

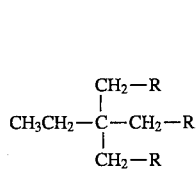 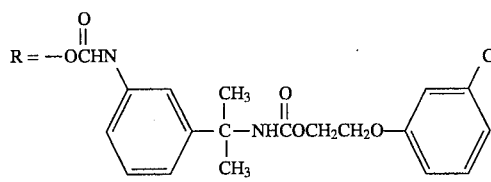 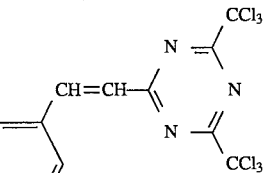

Preparation XX

This preparation illustrates the reaction of 2,4-bis(trichloromethyl)-6-[3-(2-hydroxyethoxy)styryl]-1,3,5-triazine with 2,4,6-tris(6-isocyanatohexyl)isocyanurate (available from Farbenfabriken Bayer AG, under the trade name "DESMODUR N-3300") to prepare the chromophore-substituted triazine compound referred to hereinafter as [meta-MOSTOL]$_3$/DESMO. The procedure of Preparation XVII was repeated with the exception that 2,4-bis ( trichloromethyl ) -6- [ 3- (2-hydroxyethoxy) styryl]-1,3,5-triazine (14.35 g, 0.003 mole) (meta-MOSTOL) was reacted with 2,4,6-tris(6-isocyanatohexyl)isocyanurate (5.85 g, 0.01 mole). A solid product having the structural formula shown below was isolated.

[meta-MOSTOL/TDI]$_2$/EG.

A solution containing meta-MOSTOL/TDI (13.04 g, 0.02 mole), ethylene glycol (0.62 g, 0.01 mole), and dibutyltin dilaurate (0.040 g, 0.01 mole) in 100 mL of toluene was refluxed for 3 hours. The solution was filtered and the filtrate concentrated under vacuum by means of a rotary evaporator to give an oil. This oil was redissolved in toluene and poured into hexane which was being rapidly stirred. A slightly yellow solid, 12.0 g, was collected by filtration. Infrared and GPC analysis indicated that the mixture contained about 85% of the product [meta-MOSTOL/TDI]$_2$/EG, which has the structural formula shown below.

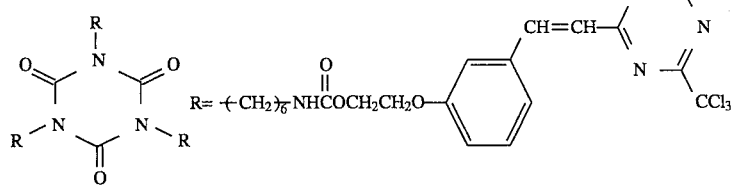

Preparations XXI–XXVII

These preparations illustrate various reactions of the product from Preparation XI, meta-MOSTOL/TDI, with a variety of diols.

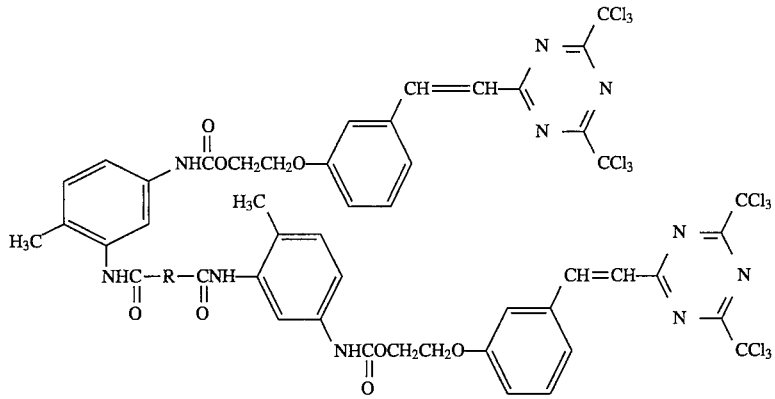

Preparation XXI

This preparation illustrates the reaction of meta-MOSTOL/TDI with ethylene glycol to prepare the chromophore-substituted triazine compound referred to hereinafter as where R represents —OCH$_2$CH$_2$O—.

Preparation XXII

This preparation illustrates the reaction of meta-MOSTOL/TDI with a polyethylene glycol having an average molecular weight of 200 to prepare the chromophore-substituted triazine compound referred to hereinafter as [meta-MOSTOL/TDI]$_2$/PEG200.

A solution containing meta-MOSTOL/TDI (5.00 g, 7.7 mmole) (product from Preparation XI), polyethylene glycol (0.77 g, 3.85 mmole, average molecular weight of 200), and dibutyltin dilaurate (0.015 g)) was refluxed for 2.5 hours. Infrared analysis indicated that the reaction was complete by disappearance of the isocyanate group. The reaction mixture was filtered and the solvent removed under vacuum by means of a rotary evaporator to give a viscous oil having the general formula shown in Preparation XXI, with the exception that R represents —O—(CH$_2$CH$_2$O—)$_n$CH$_2$CH$_2$O— n has a value of about 3.

Preparation XXIII

This preparation illustrates the reaction of meta-MOSTOL/TDI with a polyethylene glycol having an average molecular weight of 400 to prepare the chromophore-substituted triazine compound referred to hereinafter as [meta-MOSTOL/TDI]$_2$/PEG400.

The procedure of Preparation XXII was repeated with the exceptions that a polyethylene glycol having an average molecular weight of 400 was used and the reaction mixture was allowed to remain at room temperature for an additional 15 hours after reflux had been completed. The product was a viscous oil having the general formula shown in Preparation XXI, with the exception that R represents —O(CH$_2$CH$_2$O—)$_n$CH$_2$CH$_2$O— where n has a value of about 8.

Preparation XXIV

This preparation illustrates the reaction of meta-MOSTOL/TDI with a polycaprolactone diol having an average molecular weight of 540 to prepare the chromophore-substituted triazine compound referred to hereinafter as [meta-MOSTOL/TDI]$_2$/PCL540.

The procedure of Preparation XXII was repeated with the exceptions that a polycaprolactone diol having an average molecular weight of 540 was substituted for the polyethylene glycol and that the reaction mixture was refluxed for 2 hours. The product was a viscous oil having the general formula shown in Preparation XXI, with the exception that R represents a group derived from a polycaprolactone diol having an average of about four caprolactone units.

Preparation XXV

This preparation illustrates the reaction of meta-MOSTOL/TDI with a sulfonated polyester diol having an average molecular weight of 1300 to prepare the chromophore-substituted triazine compound referred to hereinafter as [meta-MOSTOL/TDI]$_2$/SPED.

The procedure of Preparation XXII was repeated with the exception that a sulfonated polyester diol, prepared from dimethyl-5-sodiumsulfoisophthalate and a polycaprolactone diol according to the procedure described in Example 9 of U.S. Pat. No. 4,408,532, and having a molecular weight of 1300. was substituted for the polyethylene glycol. The reaction product was a viscous oil having the general formula shown in Preparation XXI, with the exception that R represents the formula shown below, wherein R' represents a group derived from a polycaprolactone diol having an average of about four caprolactone units.

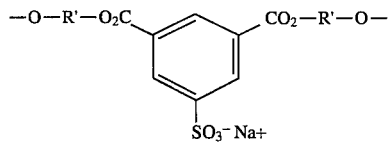

Preparation XXVI

This preparation illustrates the reaction of meta-MOSTOL/TDI with an acetylenic diol surfactant, "SURFYNOL 440" and having an average molecular weight of 382 to prepare the chromophore-substituted triazine compound referred to hereinafter as meta-MOSTOL/TDI]$_2$/ACD440.

A solution containing meta-MOSTOL/TDI (6.52 g, 0.01 mole), an acetylenic diol surfactant (1.91 g, available from Air Products and Chemicals, Inc., under the trade name "SURFYNOL 440" and having an average molecular weight of approximately 382), and dibutyltin dilaurate (0.050 g) in 40 mL of toluene was heated for 3 hours at a temperature of 60° to 65° C. Infrared analysis indicated the reaction was not completed. Additional surfactant (0.80 g) was required to react all of the isocyanate groups and complete the reaction. The solvent was removed under vacuum by means of a rotary evaporator to give approximately 9 g of a viscous oil, which was shown by infrared and GPC analysis to be consistent with a dimer product. The structural formula shown below is based on the structure of the "SURFYNOL 440" surfactant starting material, based on product literature from the supplier.

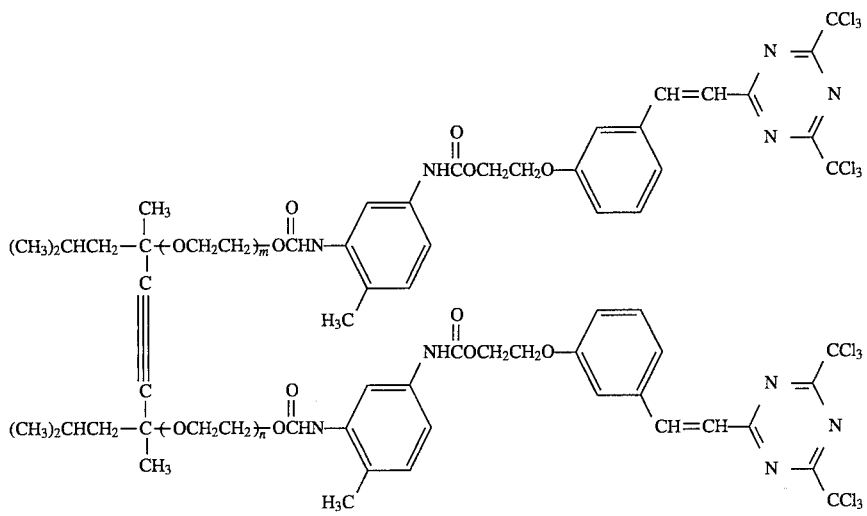

where m+n=3.5.

Preparation XXVII

This preparation illustrates the reaction of meta-MOSTOL/TDI with a acetylenic diol surfactant, "SURFYNOL 465" having an average molecular weight of 668 to prepare the chromophore-substituted triazine compound referred to hereinafter as [meta-MOSTOL/TDI]$_2$/ACD465.

The procedure of Preparation XXVI was repeated with the exception that 3.74 g of the surfactant "SURFYNOL 465" was required to react all of the isocyanate groups of the meta-MOSTOL/TDI. The product has the general formula shown in Preparation XXVI, with the exception that m+n= 10.

Preparation XXVIII

This preparation illustrates the reaction of meta-MOSTOL/TDI (Preparation XI) with 1-butanol to prepare the chromophore-substituted triazine compound referred to hereinafter as meta-MOSTOL/TDI/BUOH.

The procedure of Preparation XII was repeated, with the exception that 6.52 g (0.01 mole) of meta-MOSTOL/TDI was used and 1-butanol (0.74 g, 0.01 mole) was substituted for the polyoxyethylene nonylphenol. A light tan powder (7.03 g) having the structural formula shown below was isolated.

Preparations XXIX–XXXI

Preparations XXIX–XXXI illustrate various reactions of para-MOSTOL with a variety of dicarboxylic acids.

Preparations XXIX

This preparation illustrates the reaction of para-MOSTOL with suberic acid to prepare the chromophore-substituted triazine compound referred to hereinafter as [para-MOSTOL]$_2$/SUBERIC.

A solution containing 2,4-bis(trichloromethyl)-6-[4-(2-hydroxyethoxy)styryl]-1,3,5-triazine (MOSTOL) (9.56 g, 0.02 mole), suberic acid (1.74 g, 0.01 mole), dicyclohexylcarbodiimide (4.53 g, 0.022 g), and 4-pyrrolidinopyridine (0.150 g) in 80 mL of methylene chloride was stirred for 48 hours. GPC analysis indicated the presence of a small amount of unreacted MOSTOL. Additional methylene chloride (40 mL) was added to the mixture, and the reaction mixture was washed twice with water, then once with dilute sodium hydroxide, then once with water, and then dried with magnesium sulfate. The solvent was removed under vacuum by means of a rotary evaporator to give a viscous oil, which crystallized upon standing in a refrigerator overnight. The solid was washed with diethyl ether, filtered, and dried to give a yellow powder. For complete purification, preparative thin layer chromatography was required. The product has the structural formula shown below.

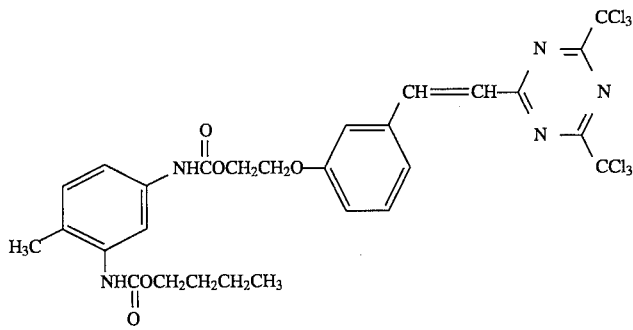

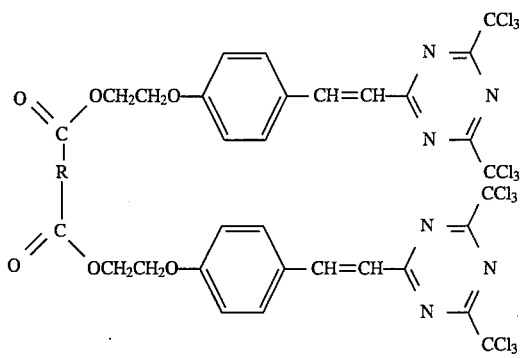

where R represents $-(CH_2)_6-$.

Preparation XXX

This preparation illustrates the reaction of para-MOSTOL with succinic acid to prepare the chromophore-substituted triazine compound referred to hereinafter as [para-MOSTOL]$_2$/SUCC.

The procedure of Preparation XXIX was repeated with the exception that succinic acid (1.18 g, 0.01 mole) was substituted for the suberic acid. A yellow solid was collected. This product was shown by infrared analysis to be consistent with a product having the formula shown in Preparation XXIX, with the exception that R represents

.

Preparation XXXI

This preparation illustrates the reaction of para-MOSTOL with terephthalic acid to prepare the chromophore-substituted triazine compound referred to hereinafter as [para-MOSTOL]$_2$/PHTH.

The procedure of Preparation XXIX was repeated with the exception that terephthalic acid (1.66 g, 0.01 mole) was substituted for the suberic acid. A yellow solid was isolated. GPC and infrared analysis indicated that the product was a 4:1 mixture of diester to monoester. Preparative thin layer chromatography was used to isolate pure product, which had the general formula shown in Preparation XXIX, with the exception that R represents a phenylene group.

The following non-limiting examples will further illustrate multilayer articles containing the photopolymerization initiators (photoinitiators) of this invention. All percentages are percentages by weight unless indicated otherwise.

EXAMPLES

Solution Preparations A, B, and C illustrate the preparation of compositions that can be used to prepare a multilayer article consisting of a release layer, a layer of photopolymerizable material, and a layer of resin.

Solution Preparation A

A solution containing the following ingredients in the amounts indicated was prepared by adding the polyvinyl alcohol resins with stirring to deionized water, which had been preheated to 190° F. After the solution had been cooled to room temperature, a surfactant and an antimicrobial agent were added.

| Ingredient | Amount (g) |
| --- | --- |
| Polyvinyl alcohol (87–89% hydrolyzed)[a] | 557 |
| Polyvinyl alcohol (98–99% hydrolyzed)[b] | 238 |
| Surfactant[c] | 20 |
| Antimicrobial agent[d] | 40 |
| Deionized water | 15,890 |

[a]"AIROL 205", Air Products and Chemicals, Inc.
[b]"AIROL 107", Air Products and Chemicals, Inc.
[c]"SURFACTOL 365", CasChem, Inc.
[d]"KATHON CG/ICP", Rohm and Haas Company This solution was used to prepare the release layer of the article.

Solution Preparation B

A solution containing the following ingredients in the amounts indicated was prepared:

| Ingredient | Amount (g) |
| --- | --- |
| Acrylic resin latex, 45% in water[a] | 10,943 |
| Polymethylmethacrylate beads, 30% in water[b] | 30 |
| Deionized water | 3,127 |

[a]"SYNTHEMUL 97603", Reichhold Chemicals, Inc.
[b]9 microns in diameter

This solution was used to prepare the layer of resin of the article.

Solution Preparation C

A master solution was prepared by combining the following ingredients in the amounts indicated with stirring.

| Ingredient | Amount (g) |
| --- | --- |
| Copolymer of 85% methyl methacrylate/ 15% methacrylic acid in methyl ketone (33% solids)[a] | 68.1 |
| Trimethylol propane triacrylate | 21.0 |
| Methyl ethyl ketone | 255.0 |

[a]This ingredient was prepared by purging a solution containing 85 g of methyl methacrylate, 15 g of methacrylic acid, and 0.400 g of 2,2'-azobisisobutyronitrile in 200 g of methyl ethyl ketone with nitrogen, sealing the reaction bottle, and heating for 22 hours.

Aliquots of this solution were used in the preparation of the photopolymerizable compositions of Examples 1–6 and Comparative Examples A–G.

Developer Solution 1

A solution was prepared by combining the following ingredients in the amounts indicated, with stirring.

| Ingredient | Amount (g) |
| --- | --- |
| Trisodium phosphate | 50 |
| Sodium dihydrogen phosphate | 10 |
| Surfactant ("PELEX NBL", Kao Corporation) | * |
| Butyl "CELLOSOLVE" | 140 |
| Water | ** |

*4 mL
**2 L

Examples 1–6 and Comparative Examples A–G

These examples describe the preparation of multilayer articles having a layer of photopolymerizable material containing a chromophore-substituted halomethyl-1,3,5-triazine photoinitiator. These examples illustrate that the compounds of Preparations III, XII, XXII, XVIII, XXIX, and XXX resist migration to a layer adjacent to the layer of photopolymerizable material.

Thirteen different solutions for preparing layers of photopolymerizable material were prepared by dissolving the amount of photoinitiator shown in Table 7 in an aliquot (11.5 g) of the master solution of Solution Preparation C.

Multilayer articles were prepared according to the following procedure:

Layer 1: The composition described in Solution Preparation A was machine coated onto a clear 2.0 mil polyester film and dried to give a release layer having a dry coating weight of 0.080 to 0.100 g/ft$^2$.

Layer 2: Each photopolymerizable composition of Examples 1–6 and Comparative Examples A–G was coated onto a separate release layer of Layer 1 by means of a #6 wire wound rod and dried for 2 minutes at a temperature of 160° F. to give a layer of photopolymerizable material having a dry coating weight of 0.090 to 0.110 g/ft$^2$.

Layer 3: The composition described in Solution Preparation B was then coated onto each of the layers of photopolymerizable material of Layer 2 by means of a #6 wire wound rod and dried at a temperature of 160° F. for 2 minutes to give a layer of resin having a dry coating weight of 0.500 to 0.700 g/ft$^2$.

The coated sheets of Examples 1–6 and Comparative Examples A–G were tested for migration of photoinitiator according to the following procedure:

Each individual sample, which had dimensions of approximately 3 inches wide by 24 inches long, was laminated to an opaque, white base (3M "MATCHPRINT" Basecommercial, Minnesota Mining and Manufacturing Company), by means of a laminator (3M MR 447 "MATCHPRINT" Minnesota Mining and Manufacturing Company), whereby the layer of resin was in contact with the white base, the laminate allowed to cool, and the polyester film, which was a carrier, was removed by stripping from the laminate with fracture occurring at the release layer/polyester film interface. A portion of the laminate was exposed for 25 seconds with a Berkey vacuum exposure frame fitted with a 5 kw combination bulb, while another portion was masked with an opaque sheet and left unexposed.

Each exposed sample was processed with Developer Solution 1. The unpolymerized material was removed by wiping with a cotton pad. In the exposed areas, the release layer (Layer 1) was washed off and the layer of photopolymerized material (Layer 2) and layer of resin (Layer 3) remained. In the masked areas, which were unexposed, the release layer (Layer 1) and the layer of photopolymerizable material (Layer 2) were washed off during processing with only the layer of resin (Layer 3) remaining adhered to the white base. The area of adhered resin constituted Background Area A for testing purposes. One-half of Background Area A of the sample was then further exposed for 50 seconds to create a portion referred to as Background Area B. The purpose of this additional exposure was to simulate the multiple exposures given to the lowest layer as additional sheets are superimposed in the process of making a surprint proof. The additional exposure also reveals the presence of a photoinitiator which may not itself have observable color, but produces colored photoproducts.

A spectrophotometer (Gretag SPM 100. available from Gretag Aktiengesellschaft of Zurich, Switzerland, and designed to measure color space based on CIELAB L*a*b* color difference), was used to measure background discoloration resulting from migration of photoinitiator. The difference between the b* value for background color (in Background Area A and Background Area B) and the b* value of the white base color, referred to herein as Δb*, was found to be a guideline for measuring the extent of migration of photoinitiator. A value of Δb* greater than one is generally considered to be clearly visible.

TABLE 7

| Example | Identity of triazine photoinitiator | Amount of photo-initiator (g) | Δb* Background Area A | Δb* Background Area B |
|---|---|---|---|---|
| Comparative A | ethyl Michler's ketone[a] | 0.050 | 0.20 | 4.18 |
| Comparative B | ethyl Michler's ketone/2,4-bis(trichloromethyl)-6-methyl-1,3,5-triazine[a] | 0.025/0.050 | 2.37 | 1.50 |
| Comparative C | 2-(4-styrylphenyl)4,6-bis(trichloromethyl)-1,3,5-triazine[b] | 0.075 | 2.38 | 1.26 |
| Comparative D | 2-(4-methoxynaphth-1-yl)-4,6-bis(trichloromethyl)-1,3,5-triazine[c] | 0.050 | 1.34 | 1.08 |
| Comparative E | 2-(4-acetoamidostyryl)-4,6-bis(trichloromethyl)-1,3,5-triazine[d] | 0.050 | 4.48 | 1.95 |
| Comparative F | 2-(4-(2-hydroxyethoxy)-styryl)-4,6-bis(trichloromethyl)-1,3,5-triazine[e] (Preparation I) | 0.075 | 2.97 | 1.72 |
| Comparative G | 2-(3-(2-hydroxyethoxy)-styryl)-4,6-bis(trichloromethyl)-1,3,5-triazine[e] (Preparation X) | 0.075 | 0.07 | 1.25 |
| 1 | para-MOSTOL/TDI/POENP5 (Preparation III) | 0.169 | 0.74 | 0.31 |
| 2 | meta-MOSTOL/TDI/POENP5 (Preparation XII) | 0.169 | 0.03 | 0.30 |
| 3 | meta-MOSTOL/TDI/PEG 200 (Preparation XXII) | 0.134 | 0.05 | 0.07 |
| 4 | [meta-MOSTOL]$_2$/TDI (Preparation XVIII) | 0.050 | 0.05 | 0.05 |
| 5 | [para-MOSTOL]$_2$/SUBERIC (Preparation XXIX) | 0.043 | 0.33 | 0.12 |
| 6 | para-MOSTOL]$_2$/SUCC (Preparation XXX) | 0.043 | 0.43 | 0.39 |

[a]Photoinitiator is disclosed in U.S. Pat. No. 4,933,452
[b]Photoinitiator is disclosed in U.S. Pat. No. 4,619,998
[c]Photoinitiator is disclosed in U.S. Pat. No. 4,189,323
[d]Photoinitiator is disclosed in U.S. Pat. No. 3,987,037; U.S. Pat. No. 4,476,215; U.S. Pat. No. 4,826,753

TABLE 7-continued

| Example | Identity of triazine photoinitiator | Amount of photo- initiator (g) | Δb* Back- ground Area A | Δb* Back- ground Area B |
|---|---|---|---|---|

<sup>e</sup>Photoinitiator is disclosed in U.S. Pat. No. 3,987,037; U.S. Pat. No. 4,826,753

The Δb* values set forth in Table 7 for Background Area A and Background Area B in Examples 1–6 and Comparative Examples A–G were calculated by the spectrophotometric method described above. The background discoloration observed with the photoinitiators of Comparative Examples A–G clearly result from migration of the photoinitiator into the layer of resin contiguous to the layer of photopolymerizable material. The photoinitiators of Examples 1–6, which are ballasted derivatives of the photoinitiators of Comparative Examples F and G, produce much lower Δb* values than the photoinitiators of Comparative Examples A–G, which indicates greater resistance to migration of the photoinitiator to the contiguous layer of resin.

The photoinitiator in the articles of Comparative Examples A and G can be detected in the layer of resin by the colored photoproducts produced during the additional exposure of Background Area B. The presence of the photoinitiators in the background area of the articles of Comparative Examples B through F is readily detectable without additional exposure.

The photoinitiator system of Comparative Examples A and B illustrate the use of a separate sensitizing dye, such as ethyl Michler's ketone, which is described in U.S. Pat. No. 4,933,452, in conjunction with a triazine photoinitiator in order to extend the sensitivity of the photoinitiator to a useable wavelength. Significant background staining was clearly evident on account of migration of the sensitizing dye itself.

Solution Preparation D

A master solution was prepared by combining the following ingredients in the amounts indicated with stirring.

| Ingredient | Amount (g) |
|---|---|
| Styrene-acrylic resin (10% in 2-butanone)<sup>a</sup> | 20.0 |
| Urethane oligomer (60% in 1-methoxy-2-propanol)<sup>b</sup> | 1.1 |
| Acidified polyvinyl butyral resin<sup>c</sup> | 8.5 |
| Pigment dispersion<sup>d</sup> | 67.8 |
| 1-Methoxy-2-propanol | 103.5 |

<sup>a</sup>"JONCRYL 67" styrene-acrylic resin, S. C. Johnson and Son, Inc.
<sup>b</sup>The oligomer was prepared according to Preparation II, U.S. Pat. No. 4,304,923
<sup>c</sup>See assignee's copending application, U.S. Ser. No. 07/716,317, filed June 17, 1991
<sup>d</sup>The dispersion contained 4.07 g of magenta pigment (Magenta Sun 234-0071, Sun Company, Inc.); 2.71 g of acidified polyvinyl butyral resin (U.S. Ser. No. 07/716,317, filed June 17, 1991), and 61.02 g of 1-methoxy-2-propanol.

Aliquots of the master solution were used in the preparation of the photopolymerizable compositions of Examples 7–11 and Comparative Example H.

Solution Preparation E

A solution containing the following ingredients in the amounts indicated was prepared:

| Ingredient | Amount (g) |
|---|---|
| Polyvinyl acetate resin latex, 50% in water<sup>a</sup> | 250.0 |
| Polymethylmethacrylate beads, 30% in water<sup>b</sup> | 0.9 |
| Deionized water | 250.0 |

<sup>a</sup>"WALLPOL" Synthetic Resin Emulsion 40-100, Reichhold Chemicals, Inc.
<sup>b</sup>6 microns in diameter This solution was used to prepare the layer of resin of the article.

Examples 7–11 and Comparative Example H

These examples describe the preparation of multilayer articles having a layer of photopolymerizable material containing a chromophore-substituted halomethyl-1,3,5-triazine photoinitiator. These examples illustrate that ballasted photoinitiators of Preparation III, and V–VIII of this invention resist migration into a layer adjacent to the layer of photopolymerizable material. The compounds of Preparations III, and V-VIII are TDI/polyoxyethylene nonylphenol derivatives of the compound of Preparation I, para-MOSTOL, but they vary in molecular weight.

Six separate coating solutions for preparing layers of photopolymerizable material were prepared by predissolving each of the triazine photoinitiators shown in Table 8 in the amount shown in 1-methoxy-2-propanol (2.0 g) and then adding an aliquot (13.2 g) of the master solution from Solution Preparation D. With increasing molecular weight of the photoinitiator, the amount of photoinitiator added was increased to provide an equivalent weight of the parent moiety (i.e., the compound of Preparation I) in the coating solution of each example.

TABLE 8

| Example | Triazine photoinitiator | Molecular weight | Amount (g) |
|---|---|---|---|
| Comparative H | Preparation I | 478 | 0.050 |
| 7 | Preparation V | 960 | 0.100 |
| 8 | Preparation III | 1,078 | 0.113 |
| 9 | Preparation VI | 1,401 | 0.146 |
| 10 | Preparation VII | 2,634 | 0.276 |
| 11 | Preparation VIII | 5,277 | 0.552 |

Multilayer articles were prepared according to the following procedure:

Layer 1: The composition described in Solution Preparation A was machine coated onto a clear 2.0 mil polyester film and dried to give a release layer having a dry coating weight of 0.80 to 1.00 g/ft².

Layer 2: Each photopolymerizable composition of Examples 7–11 and Comparative Example H was coated onto a separate release layer of Layer 1 by means of a #6 wire wound rod and dried for 2 minutes at a temperature of 160° F. to give a layer of photopolymerizable material containing magenta pigment and having a dry coating weight of 0.100 to 0.120 g/ft².

Layer 3: The composition described in Solution Preparation E was then coated onto each of the layers of photopolymerizable material by means of a #4 wire wound rod and dried at a temperature of 160° F. for 2 minutes to give a layer of resin having a dry coating weight of 0.500 to 0.700 g/ft².

The coated sheets of Examples 7–11 and Comparative Example H were tested for migration of photoinitiator according to the testing procedure used for Examples 1–6, with the exceptions noted below:

Each individual sample, which had dimensions of approximately 3 inches wide by 24 inches long, was laminated to an opaque, white base (3M "MATCHPRINT" Basecommercial, Minnesota Mining and Manufacturing Company), by means of a laminator (3MMR 447 "MATCHPRINT" Minnesota Mining and Manufacturing Company), whereby the layer of resin was in contact with the white base, the laminate allowed to cool, and the polyester film, which served as a carrier, was removed by stripping from the laminate with fracture occurring at the release layer/polyester film interface. A portion of the laminate was exposed for 40 seconds through a 21-step photographic step wedge with a Berkey vacuum exposure frame fitted with a 5 kw combination bulb, while another portion was masked with an opaque sheet and left unexposed.

Each exposed sample was then passed through a rotary brush processor containing an aqueous solution of 1% $K_2CO_3$, 1% $KHCO_3$, and 0 1% surfactant ("SURFYNOL 465" Air Products and Chemicals, Inc.) maintained at a temperature of 80° F. In the exposed areas, the release layer (Layer 1) was washed off and the layer of photopolymerized material, i.e., having a magenta image (Layer 2), and layer of resin (Layer 3) remained. The number of grey-scale steps reproduced in the photopolymerized magenta area from the step wedge was recorded. In the masked areas, which were unexposed, the release layer (Layer 1) and the layer of photopolymerizable material (Layer 2) were washed off during processing, and only the layer of resin (Layer 3) remained adhered to the white base, which would constitute Background Area A for testing purposes. One-half of Background Area A of the sample was then further exposed for 50 seconds to create a portion referred to as Background Area B.

Background Areas A and B of each sample were visually inspected for evidence of background staining, which would result from migration of the triazine photoinitiator from the layer of photopolymerizable material into the layer of resin. The results are set forth in Table 9.

TABLE 9

| Example | Preparation | Compound* | Wedge exposure steps | Staining Area A | Staining Area B |
|---|---|---|---|---|---|
| Comparative H | I | para-MOSTOL | 5 | yes | yes |
| 7 | V | para-MOSTOL/TDI/POENP2 | 6 | no | no |
| 8 | III | para-MOSTOL/TDI/POENP5 | 6 | no | no |
| 9 | VI | para-MOSTOL/TDI/POENP12 | 5.5 | no | no |
| 10 | VII | para-MOSTOL/TDI/POENP40 | 3.5 | no | no |
| 11 | VIII | para-MOSTOL/TDI/POENP100 | 2 | no | no |

*For the identities of the compounds (adducts) listed, the acronym POENPX means polyoxyethylene nonylphenol having a mole ratio of X, where X is a number equal to the mole ratio of the polyoxyethylene nonylphenol.

A yellow stain was clearly evident in Background Areas A and B of Comparative Example H on account of migration of the compound of Preparation I, para-MOSTOL. However, the articles of Examples 7–11, which contained the compounds of the invention from Preparation III, V, VI, VII, and VIII, i.e., ballasted derivatives of para-MOSTOL, did not show any evidence of yellow background stain, which is evidence of resistance to migration of the photoinitiators.

Examples 12–13 and Comparative Example J

These examples describe the preparation of multilayer articles having a layer of photopolymerizable material containing a chromophore-substituted halomethyl-1,3,5-triazine photoinitiator. These examples illustrate that ballasted compounds of Preparations XII–XIII of this invention do resist migration into a layer adjacent to the layer of photopolymerizable material. The compounds of Formulae XII–XIII are TDI/polyoxyethylene nonylphenol derivatives of the compound of Preparation IX.

The procedures used in the preparation and evaluation of Examples 7–11 and Comparative Example H were repeated, with the exception that the compounds of Preparations IX, XII, and XIII listed in Table 10 were used in the preparation of the layer of photopolymerizable material (Layer 2).

TABLE 10

| Example | Triazine photoinitiator | Molecular weight | Amount (g) |
|---|---|---|---|
| Comparative J | Preparation IX | 478 | 0.050 |
| 12 | Preparation XII | 960 | 0.100 |
| 13 | Preparation XIII | 1,078 | 0.114 |

The results of the visual inspection of Examples 12–13 and Comparative Example J are set forth in Table 11.

TABLE 11

| Example | Preparation | Compound | Wedge exposure steps | Staining Area A | Staining Area B |
|---|---|---|---|---|---|
| Comparative J | IX | meta-MOSTOL | 4 | no | yes |
| 12 | XII | meta-MOSTOL/TDI/POENP2 | 6.5 | no | no |
| 13 | XIII | meta-MOSTOL/TDI/POENP5 | 6.5 | no | no |

Because the parent compound of Preparation IX, meta-MOSTOL, is essentially colorless, staining in Background Area A was not detected. However, upon further exposure, a discoloration of Background Area. B was noted. This discoloration apparently resulted from photodecomposition products of meta-MOSTOL, which migrated into the background area. No background discoloration was noted in the background areas of the articles of Examples 12 and 13, thereby clearly indicating that little or no migration occurred when ballasted meta-MOSTOL derivatives were used.

Examples 14–17

These examples describe the preparation of multilayer articles having a layer of photopolymerizable material containing a chromophore-substituted halomethyl-1,3,5-triazine photoinitiator. These examples illustrate that the ballasted compounds of Preparations XIV–XVII of this invention resist migration into a layer adjacent to the layer of photopolymerizable material. The compounds of Preparations XIV–XVII are dimers or trimers prepared from diisocyanates and triisocyanates and the compound of Preparation I or Preparation IX.

The procedures used in the preparation and evaluation of the articles of Examples 7–11 were repeated, with the exception that compounds of Preparations XIV–XVII listed in Table 12 were used in the preparation of the layers of photopolymerizable material (Layer 2).

TABLE 12

| Example | Triazine photoinitiator | Molecular weight | Amount (g) |
|---|---|---|---|
| 14 | Preparation XIV | 1,130 | 0.059 |
| 15 | Preparation XV | 1,130 | 0.092 |
| 16 | Preparation XVI | 1,178 | 0.092 |
| 17 | Preparation XVII | 1,938 | 0.068 |

The results of the visual inspection of the articles of Examples 14–17 are set forth in Table 13.

TABLE 13

| Example | Prepara- tion | Compound* | Wedge exposure steps | Staining Area A | Area B |
|---|---|---|---|---|---|
| 14 | XIV | [meta-MOSTOL]$_2$/TDI | 6.5 | no | no |
| 15 | XV | [para-MOSTOL]$_2$/TDI | 5.0 | no | no |
| 16 | XVI | [meta-MOSTOL]$_2$/IPDI | 4.0 | no | no |
| 17 | XVII | [meta-MOSTOL]$_2$/CYTH | 6.5 | no | no |

No background discoloration was noted in the articles of Examples 14–17, i.e., those containing ballasted meta-MOSTOL derivatives. The results clearly indicated that little or no migration of the photoinitiator to an adjacent layer occurred.

Examples 18–21

Examples 18–21 describe the preparation of multilayer articles having a layer of photopolymerizable material containing a chromophore-substituted halomethyl-1,3,5-triazine photoinitiator. These examples illustrate that the ballasted compounds of Preparations XXII–XXV of this invention resist migration into a layer adjacent to the layer of photopolymerizable material. The compounds of Preparation XXII–XXV are derivatives of the compound of Preparation X and a variety of diols.

The procedures used in the preparation and evaluation of the articles of Examples 7–11 were repeated, with the exception that the compounds of Preparations XXII–XXV listed in Table 14 were used in the preparation of the layer of photopolymerizable material (Layer 2).

TABLE 14

| Example | Triazine photoinitiator | Molecular weight | Amount (g) |
|---|---|---|---|
| 18 | Preparation XXII | 1,504 | 0.089 |
| 19 | Preparation XXIII | 1,704 | 0.110 |
| 20 | Preparation XXIV | 1,838 | 0.124 |
| 21 | Preparation XXV | 2,544 | 0.111 |

The results of the visual inspection of the articles of Examples 18–21 are set forth in Table 15.

TABLE 15

| Example | Prepara- tion | Compound | Wedge exposure steps | Staining Area A | Area B |
|---|---|---|---|---|---|
| 18 | XVIII | meta-MOSTOL/TDI/PEG200 | 7.5 | no | no |
| 19 | XIX | meta-MOSTOL/TDI/PEG400 | 7.5 | no | no |
| 20 | XX | meta-MOSTOL/TDI/PCL540 | 7.5 | no | no |
| 21 | XXV | meta-MOSTOL/TDI/SPD | 6.5 | no | no |

No background discoloration was noted in the articles of Examples 18–21, i.e., those containing ballasted meta-MOSTOL derivatives. The results clearly indicated that little or no migration of the photoinitiator occurred.

Solution Preparation F

A master solution containing the ingredients shown in the amounts indicated was prepared.

| Ingredient | Amount (g) | Solids (%) | Solvent |
|---|---|---|---|
| Styrene-acrylic resin[a] | 21.8 | 50.0 | 2-butanone |
| Urethane oligomer[b] | 168.2 | 61.0 | 2-butanone |
| Acidified polyvinyl butyral[c] | 26.0 | 21.0 | 2-butanone |
| Pigment dispersion[d] | 232.0 | 15.0 | 3-methoxypropanol |
| 2-Butanone | 401.0 | | |

-continued

| Ingredient | Amount (g) | Solids (%) | Solvent |
|---|---|---|---|
| 1-Methoxy-2-propanol | 35. | | |
| Total | 884.1 | 17.39 | | a"JONCRYL 67" styrene-acrylic resin, S. C. Johnson and Son, Inc.
bThe oligomer was prepared according to Preparation II, U.S. Pat. No. 4,304,923
cSee assignee's copending application, U.S. Ser. No. 07/716,317, filed June 17, 1991
dThe dispersion contained 19.50 g magenta pigment (Magenta Sun 234-0071, Sun Company, Inc.); 2.61 g polyvinyl butyral resin ("BUTVAR B-98", Monsanto Company); 10.37 g acrylic resin ("JONCRYL 67"); 0.38 g surfactant ("FLUORAD FC-430", Minnesota Mining and Manufacturing Company); 1.95 g dispersant ("DISPERBYK-161", BYK-Chemie); and 197.0 g 1-methoxy-2-propanol Examples 22–29 and Comparative Examples K–L These examples describe the preparation of multilayer articles having a layer of photopolymerizable material containing a chromophore-substituted halomethyl-1,3,5-triazine photoinitiator. These examples illustrate that the ballasted compounds of Preparations III, XII, XVIII, XXII, XXVI, XXVII, XXX, and XXXI of this invention resist migration into a layer adjacent to the layer of photopolymerizable material.

Each of the triazine photoinitiators listed in Table 16 in the amounts indicated were predissolved in 2-butanone (1.0 g) and added to aliquots (8.90 g) of Solution Preparation F to prepare a series of coating compositions for preparing layers of photopolymerizable material. The amount of each photoinitiator was adjusted on the basis of molecular weight to provide an equivalent weight of the halomethyl-1,3,5-triazine moiety. These compositions were coated and processed in the manner described in Example 7–11, with the exception that Solution Preparation B was substituted for Solution Preparation E for coating Layer 3. A slight amount of magenta pigment remained in the background areas of all of the samples. Because some pigment was retained in the background, a control sheet that was free of photoinitiator in the layer of photopolymerizable material was made. The coated sheet was processed in exactly the same manner as was the article containing photoinitiator in the layer of photopolymerizable material and used as a control for determining background discoloration.

The backgrounds of the articles of Examples 22–29 and Comparative Examples K–L were compared with the background of the control sheet by visual inspection and with a spectrophotomer. The spectrophotometric method was carried out in the same manner as described in Examples 1–6 and Comparative Examples A–G, with the exception that $\Delta b^*$ is the difference between the b* value of the background of the article of the example and the b* value of the background of the control sheet. The results are shown in Table 16.

TABLE 16

| Example | Photo-initiator | Amount (g) | Im-aged steps | Visual stain-ing | Δb* Area A | Δb* Area B |
|---|---|---|---|---|---|---|
| Comparative K | 2-(4-(2-hydroxyethoxy)styryl)-4,6-bis(trichloromethyl)-1,3,5-triazine (Preparation I) | 0.080 | 1 | yes | 2.67 | 1.90 |
| Comparative L | 2-(3-(2-hydroxyethoxy)styryl)-4,6-bis(trichloromethyl)-1,3,5-triazine (Preparation X) | 0.080 | 5 | no | 0.18 | 0.90 |
| 22 | para-MOSTOL/TDI/POENP5 (Preparation III) | 0.184 | 5 | no | 0.68 | 0.21 |
| 23 | [para-MOSTOL]₂/PHTH (Preparation XXXI) | 0.043 | 2 | no | 0.84 | 0.30 |
| 24 | meta-MOSTOL/TDI/BUOH (Preparation XVIII) | 0.122 | 7 | no | 0.00 | 0.20 |
| 25 | [meta-MOSTOL/TDI/POENP5 (Preparation XII) | 0.184 | 4 | no | −0.07 | 0.04 |
| 26 | [meta-MOSTOL/TDI]₂/PCL-540 (Preparation XXIV) | 0.153 | 3 | no | 0.16 | 0.19 |
| 27 | [meta-MOSTOL/TDI]₂/SURF 440 (Preparation XXVI) | 0.109 | 7 | no | −0.01 | −0.02 |
| 28 | [meta-MOSTOL]₂/IPDI (Preparation XVII) | 0.099 | 2 | no | 0.15 | −0.06 |
| 29 | meta-MOSTOL]₃/DESMO (Preparation XX) | 0.108 | 5 | no | −0.10 | −0.18 |

The presence of discoloration in the background is clearly evident in the article of Comparative Example K. The photoinitiators used in the articles of Examples 22 and 23, which are ballasted derivatives of the photoinitiator of Preparation I, which was used in the article of Comparative Example K, produced much lower Δb* values than did the article of Comparative Example K, which is evidence of reduced migration of photoinitiator. Although no discoloration of the background was observed in the article of Comparative Example L, the presence of migration was detected by the Δb* value of 0.90. This value is significantly higher than the values observed with the ballasted compounds used in the articles of Examples 24–29, which did not show visual evidence of discoloration and exhibited low values of Δb*, which is evidence that negligible amounts of the compounds of Preparations III, XII, XVIII, XXIV, XXVI, XXVII, XXX, and XXXI migrated to the layer adjacent to the layer of photopolymerizable material.

Solution Preparations G, H, J, and K

Four master solutions were prepared by combining the ingredients shown in Table 17 in the amounts indicated, with stirring. Aliquots of these solutions were used in the preparation of the photopolymerizable compositions of Solution Preparations M through LL.

TABLE 17

| | | Solution Preparation | | | |
|---|---|---|---|---|---|
| Ingredient | Concentration (%) | G (Yellow) Amount (g) | H (Cyan) Amount (g) | J (Magenta) Amount (g) | K (Black) Amount (g) |
| Urethane oligomer in 2-butanone[a] | 64.4 | 29.66 | 57.63 | 45.25 | 34.8 |
| Acidified polyvinyl butyral resin in 2-butanone[b] | 23.4 | 13.31 | 7.72 | 7.19 | 14.73 |
| Styrene-acrylic resin in 2-butanone[c] | 35.0 | — | 11.08 | 9.01 | 1.94 |
| Yellow pigment dispersion | 18.9 | 53.97 | — | — | — |
| Cyan pigment dispersion | 19.2 | — | 41.57 | — | — |
| Magenta pigment dispersion | 24.0 | — | — | 41.72 | — |
| Black pigment dispersion | 28.2 | — | — | — | 49.84 |
| 2-Butanone | — | 111.5 | 82.6 | 108.7 | 88.2 |
| 1-Methoxy-2-propanol | — | 43.9 | 20.0 | 23.4 | 24.7 |

[a]This solution was prepared according to Preparation II, U.S. Pat. No. 4,304,923
[b]See assignee's copending application, U.S. Ser. No. 07/716,317, filed June 17, 1991
[c]"JONCRYL 67" styrene-acrylic resin, S. C. Johnson and Son, Inc.

The pigment dispersions set forth in Table 18 contained the following ingredients in the amounts indicated.

TABLE 18

| Ingredient | Yellow pigment dispersion Amount (g) | Cyan pigment dispersion Amount (g) | Magenta pigment dispersion Amount (g) | Black pigment dispersion Amount (g) |
|---|---|---|---|---|
| Yellow pigment (Mobay YB-5785, Mobay Corp.) | 5.93 | — | — | — |
| Cyan pigment (Sun 249-0592, Sun Company, Inc.) | — | 4.64 | — | — |
| Magenta pigment (Sun 234-0071, Sun Company, Inc.) | — | — | 5.60 | — |
| Black pigment (Raven 760, Columbia Chemicals Co.) | — | — | — | 7.78 |
| Polyvinyl butyral resin ("BUTVAR B-98", Monsanto Company) | 1.38 | 1.55 | 0.75 | 1.39 |
| Styrene-acrylic resin ("JONCRYL 67", S. C. Johnson and Son, Inc.) | 2.57 | 1.55 | 2.99 | 4.16 |
| Dispersant ("DISPERBYK-161", BYK-Chemie) | 0.30 | 0.23 | 0.56 | 0.69 |
| Surfactant ("FLUORAD FC-430", Minnesota Mining and Manufacturing Company) | 0.02 | 0.02 | 0.02 | 0.03 |
| 2-Butanone | 26.30 | 20.10 | 19.00 | — |
| 1-Methoxy-2-propanol | 17.50 | 13.40 | 4.00 | 35.80 |

Solution Preparation L

A master solution containing the following ingredients in the amounts indicated was used to prepare the composition for the photopolymerizable barrier layer (Layer 3) of the articles of Comparative Examples M–P and Examples 30–45.

| Ingredient | Amount (g) |
|---|---|
| Triacrylated aromatic epoxide (20% in 2-butanone)[a] | 36.0 |
| Styrene-acrylic resin (50% in 2-butanone)[b] | 4.8 |
| Surfactant (10% in 2-butanone)[c] | 0.3 |
| 2-Butanone | 200.0 |

[a]Echo Resin "TAE" #310, Echo Resins and Laboratory
[b]"JONCRYL 67" styrene-acrylic resin, S. C. Johnson and Son, Inc.
[c]"FLUORAD FC-430", Minnesota Mining and Manufacturing Company Solution Preparations M–LL Separate photopolymerizable compositions were prepared by dissolving the specific triazine photoinitiator in the amount indicated in 10.00 g of the master solution of Solution Preparations G, H, J, K, and L, as shown in Table 19. These solutions were used in the preparation of the multilayer articles of Comparative Examples M–P and Examples 30–45.

TABLE 19

| Solution Preparation | Triazine photo-initiator | Amount of triazine photoinitiator added to 10.00 g aliquots of Solution Preparation (g) | | | | |
|---|---|---|---|---|---|---|
| | | G (yellow) | H (cyan) | J (magenta) | K (black) | L (barrier) |
| M | Preparation IX | 0.150 | — | — | — | — |
| N | Preparation IX | — | 0.063 | — | — | — |
| O | Preparation IX | — | — | 0.031 | — | — |
| P | Preparation IX | — | — | — | 0.221 | — |
| Q | Preparation IX | — | — | — | — | 0.014 |
| R | Preparation XII | 0.150 | — | — | — | — |
| S | Preparation XII | — | 0.063 | — | — | — |
| T | Preparation XII | — | — | 0.031 | — | — |
| U | Preparation XII | — | — | — | 0.221 | — |
| V | Preparation XII | — | — | — | — | 0.014 |
| W | Preparation XVIII | 0.177 | — | — | — | — |
| X | Preparation XVIII | — | 0.075 | — | — | — |
| Y | Preparation XVIII | — | — | 0.037 | — | — |
| Z | Preparation XVIII | — | — | — | 0.261 | — |
| AA | Preparation XVIII | — | — | — | — | 0.017 |
| BB | Preparation XX | 0.202 | — | — | — | — |
| CC | Preparation XX | — | 0.085 | — | — | — |
| DD | Preparation XX | — | — | 0.042 | — | — |
| EE | Preparation XX | — | — | — | 0.298 | — |
| FF | Preparation XX | — | — | — | — | 0.019 |
| GG | Preparation XXII | 0.150 | — | — | — | — |
| HH | Preparation XXII | — | 0.063 | — | — | — |
| JJ | Preparation XXII | — | — | 0.031 | — | — |
| KK | Preparation XXII | — | — | — | 0.221 | — |
| LL | Preparation XXII | — | — | — | — | 0.014 |

Solution Preparation MM

A solution containing the following ingredients in the amounts indicated was prepared:

| Ingredient | Amount (g) |
|---|---|
| Acrylic resin latex, 45% in water[a] | 100.0 |
| Polymethylmethacrylate beads, 30% in water[b] | 0.4 |
| Surfactant[c] | 0.2 |
| Deionized water | 50.0 |

[a] "SYNTHEMUL 97603", Reichhold Chemicals, Inc.
[b] 9 microns in diameter
[c] "FLUORAD FC-120", Minnesota Mining and Manufacturing Company This solution was used to prepare the layer of resin of the article.

Comparative Examples M–P and Examples 30–49

These examples illustrate the preparation of a surprint proof by successively superimposing four pigment-containing multilayer articles having a layer of photopolymerizable material containing a chromophoresubstituted halomethyl-1,3,5-triazine photoinitiator. These examples illustrate that the ballasted compounds of Preparations IX, XVIII, XX, and XXII of this invention resist migration into an adjacent layer.

Multilayer articles of Examples 30–33 and Comparative Example M were prepared by coating the Solution Preparations set forth in Table 20 according to the following procedure:

Layer 1: The composition described in Solution Preparation A was machine coated onto a clear 2.0 mil polyester film and dried to give a release layer having a dry coating weight of 0.080 to 0.100 g/ft$^2$.

Layer 2: Each pigment-containing photopolymerizable composition of Solution Preparations M–P, R–U, W–Z, BB–EE, and GG, HH, JJ, KK was coated onto a release layer of Layer 1 by means of a #6 wire wound rod and dried for 2 minutes at a temperature of 160° F. to give a layer of photopolymerizable material having a dry coating weight of 0.090 to 0.110 g/ft$^2$.

Layer 3: The photopolymerizable compositions of Solution Preparations Q, V, AA, FF, and LL were coated onto the appropriate layers (as shown in Table 20) of photopolymerizable material of Layer 2 by means of a #6 wire wound rod and dried at a temperature of 160° F. for 2 minutes to give a layer of photopolymerizable material having a dry coating weight of 0.035 to 0.040 g/ft$^2$.

Layer 4: The composition described in Solution Preparation MM was then coated onto each of the layers of the photopolymerizable material of Layer 3 by means of a #6 wire wound rod and dried at a temperature of 160° F. for 2 minutes to give a layer of resin having a dry coating weight of 0.500 to 0.700 g/ft$^2$.

TABLE 20

| Example | Triazine photo-initiator | Color of pigment in sheet | Solution Preparation | | | |
|---|---|---|---|---|---|---|
| | | | Layer 1 | Layer 2 | Layer 3 | Layer 4 |
| Comparative M | Preparation IX | yellow | A | M | Q | MM |
| Comparative N | Preparation IX | cyan | A | N | Q | MM |
| Comparative O | Preparation IX | magenta | A | O | Q | MM |
| Comparative P | Preparation IX | black | A | P | Q | MM |
| 30 | Preparation XII | yellow | A | R | V | MM |
| 31 | Preparation XII | cyan | A | S | V | MM |
| 32 | Preparation XII | magenta | A | T | V | MM |
| 33 | Preparation XII | black | A | U | V | MM |
| 34 | Preparation XVIII | yellow | A | W | AA | MM |
| 35 | Preparation XVIII | cyan | A | X | AA | MM |
| 36 | Preparation XVIII | magenta | A | Y | AA | MM |

TABLE 20-continued

| Example | Triazine photo-initiator | Color of pigment in sheet | Solution Preparation | | | |
|---|---|---|---|---|---|---|
| | | | Layer 1 | Layer 2 | Layer 3 | Layer 4 |
| 37 | Preparation XVIII | black | A | Z | AA | MM |
| 38 | Preparation XX | yellow | A | BB | FF | MM |
| 39 | Preparation XX | cyan | A | CC | FF | MM |
| 40 | Preparation XX | magenta | A | DD | FF | MM |
| 41 | Preparation XX | black | A | EE | FF | MM |
| 42 | Preparation XXII | yellow | A | GG | LL | MM |
| 43 | Preparation XXII | cyan | A | HH | LL | MM |
| 44 | Preparation XXII | magenta | A | JJ | LL | MM |
| 45 | Preparation XXII | black | A | KK | LL | MM |

The multilayer sheets of Comparative Examples M–P and Examples 30–45 were used to prepare the five surprint proofs of Comparative Example Q and Examples 46–50. as shown in Table 21, according to the following procedure:

The first color of the surprint proof of Example was prepared by laminating the yellow article described in Comparative Example M to an opaque, white base (3M "MATCHPRINT" Base-commercial, Minnesota Mining and Manufacturing Company) by means of a laminator (3M MR 447 "MATCHPRINT", Minnesota Mining and Manufacturing Company), whereby the layer of resin was in contact with the white base the laminate allowed to cool, and the polyester film, which was the carrier, was removed by stripping from the composite with fracture occurring at the release layer/polyester interface. A portion of the laminate was exposed for 25 seconds through a 21-step photographic step wedge with a Berkey vacuum exposure frame fitted with a 5 kw combination bulb, while another portion was masked with an opaque sheet and left unexposed. The sheet was then passed through a rotary brush processor containing an aqueous solution of 1% $K_2CO_3$, 1% $KHCO_3$, and 0.1% surfactant ("SURFYNOL 465", Air Products and Chemicals, Inc.) at a temperature of 80° F. In the exposed areas, the release layer (Layer 1) was washed off and the layer of imaged photopolymerized material, i.e., yellow image (Layer 2), the barrier layer of photopolymerized material (Layer 3), and the layer of resin (Layer 4) remained. The number of grey-scale steps reproduced in the photopolymerized yellow area is set forth in Table 21. In the masked area, the release layer (Layer 1) and the layers of photopolymerizable material (Layer 2 and Layer 3) were washed off during processing, and only the layer of resin (Layer 4) remained adhered to the base, which would constitute the background.

The cyan article of Comparative Example N was laminated onto the yellow image of the composite article and imaged by repeating the foregoing procedure. Particular care was taken to have a common masked area for each color. The magenta article of Comparative Example O was laminated onto the cyan image of the composite article and imaged. The black article of Comparative Example P was laminated onto the magenta image of the composite article and imaged to prepare a four-color surprint proof (Comparative Example Q).

Using the procedure for the preparation of the surprint proof of Comparative Example Q, the surprint proof of Example 46 was prepared from multilayer articles of Examples 30–33; the surprint proof of Example 47 from multilayer articles of Examples 33-37; the surprint proof of Example 48 from the multilayer articles of Examples 38–41; and the surprint proof of Example 49 from the multilayer articles of Examples 42–45.

The values of $\Delta b^*$ and $\Delta E$ were measured for the unexposed area, i.e., the background of the proof of Comparative Example Q and the proofs of Examples 46–49, by means of the Gretag SPM 100 spectrophotometer, as described in Examples 1–6 and Comparative Examples A–G. The background of each surprint proof was then given an overall 25 second exposure and the values of $\Delta b^*$ and $\Delta E$ remeasured. The values of $\Delta b^*$ and $\Delta E$ for the unexposed background and exposed background are set forth in Table 21.

TABLE 21

| Example | Triazine photo-initiator | Preparation | Imaged steps | Background of surprint proof | | | |
|---|---|---|---|---|---|---|---|
| | | | | unexposed | | exposed | |
| | | | | $\Delta b^*$ | $\Delta E$ | $\Delta b^*$ | $\Delta E$ |
| Comparative Q | meta-MOSTOL | IX | yellow-7 cyan-6 magenta-6 black-5 | 0.98 | 1.05 | 5.54 | 5.64 |
| 46 | meta-MOSTOL/ TDI/ POENP5 | XII | yellow-6 cyan-5 magenta-5 black-4 | 0.48 | 0.51 | 1.08 | 1.10 |
| 47 | [meta-MOSTOL]$_2$/ TDI | XVIII | yellow-7 cyan-6 magenta-7 black-6 | 0.36 | 0.42 | 1.78 | 1.73 |
| 48 | [meta-MOSTOL]$_3$/ DESMO | XX | yellow-8 cyan-6 magenta-6 black-7 | 0.35 | 0.40 | 1.01 | 1.06 |

TABLE 21-continued

| Example | Triazine photo-initiator | Prep-ara-tion | Imaged steps | Background of surprint proof | | | |
|---|---|---|---|---|---|---|---|
| | | | | unexposed | | exposed | |
| | | | | Δb* | ΔE | Δb* | ΔE |
| 49 | [meta-MOSTOL/ TDI]$_2$/ PEG200 | XXII | yellow-8 cyan-6 magenta-6 black-7 | 0.53 | 0.59 | 0.94 | 1.00 |

The photoinitiators used in Examples 46–49, which are ballasted derivatives of the photoinitiator of Preparation IX, which was used to prepare the proof of Comparative Example Q, produced significantly lower Δb* and ΔE values than did the photoinitiators of Comparative Example Q, which is evidence of their increased resistance to migration. The Δb* and ΔE values of approximately 1.00 for the unexposed background of the surprint proof of Comparative Example Q are considered indicative of a visually observable discoloration. However, the Δb* and ΔE values of about 0.50 or lower for Examples 46–49 are well below the value of 1.00 and discoloration is not visually observable. Exposure of the background produced a dramatic difference in background discoloration, which resulted from photodecomposition products of the photoinitiator that had migrated to a contiguous layer. The values of Δb* and ΔE of about 1.00 for Examples 46, 48, and 49 and about 1.80 for Example 47 are significantly lower than the values of Δb* and ΔE of about 5.60 for Comparative Example Q, which is associated with a highly visible discoloration. Therefore, the lower values of Δb* and ΔE for Examples 46– 49 as compared with those for Comparative Example Q is evidence that compounds of Preparations XII, XVIII, XX, and XXII were much more resistant to migration into the resin layer adjacent to the layer of photopolymerizable material than was the compound of Preparation IX. Also, the surprint proof prepared using the multilayer articles containing these ballasted triazine photoinitiators did not exhibit background discoloration.

In a quantitative sense, the phrase "capable of resisting migration" can mean either (1) having a Δb* for unexposed background area and for exposed background area equal to or less than 1.0 for a single sheet one-color proof or (2) having a Δb* for unexposed background area equal to or less than 1.0 and a Δb* for exposed background area equal to or less than 2.0 for a four sheet four-color proof.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A chromophore-substituted halomethyl-1,3,5-triazine photopolymerization initiator having the general formula

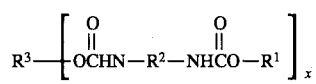

wherein:

$R^1$ represents a residue of a chromophore-substituted, halomethyl-1,3,5-triazine compound, wherein said chromophore is hydroxyl-substituted, said triazine compound having the formula $R^1$—OH, $R^2$ represents a residue of a diisocyanate compound, said diisocyanate compound having the formula $R^2(NCO)_2$, having isocyanato groups, (NCO), of dissimilar reactivities, and $R^3$ represents a residue of a hydroxyl-substituted compound, said hydroxyl-substituted compound having the formula $R^3(OH)_x$, where x represents an integer greater than or equal to 1, said compound $R^3(OH)_x$ being selected from the group consisting of aliphatic alcohols and aliphatic polyols having from 1 to 20 carbon atoms; aralkyl alcohols and aralkyl polyols having up to 3 aromatic rings in the aryl portion thereof, and from 1 to 10 carbon atoms in the alkyl portion thereof; alkyl alcohols and alkyl polyols derived from heteroaromatig or heterocyclic compounds having from 1 to 10 carbon atoms in the alkyl portion thereof.

2. A chromophore-substituted halomethyl-1,3,5-triazine photopolymerizable initiator having the general formula

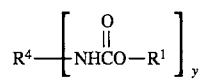

wherein $R^1$ represents a residue of a chromophore-substituted, halomethyl-1,3,5-triazine compound, wherein said chromophore is a hydroxyl-substituted chromophore, said triazine compound having the formula RLOH, and $R^4$ represents a residue of a isocyanato compound, said isocyanato compound having the formula $R^4(NCO)_y$, where y represents an integer from 2 to 4.

3. A chromophore-Substituted halomethyl-1,3,5-triazine photopolymerization initiator having the general formula

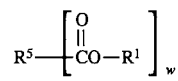

wherein $R^1$ represents a residue of a chromophore-substituted, halomethyl-1,3,5-triazine compound, wherein said chromophore is a hydroxyl-substituted chromophore, said triazine compound having the formula $R^1$—OH, and $R^5$ represents a residue of a carboxylic acid, said carboxylic acid having the formula $R^5(CO_2H)_2$, where w represents an integer greater than or equal to 2.

4. The photopolymerization initiator of claim 1, wherein $R^1$ represents

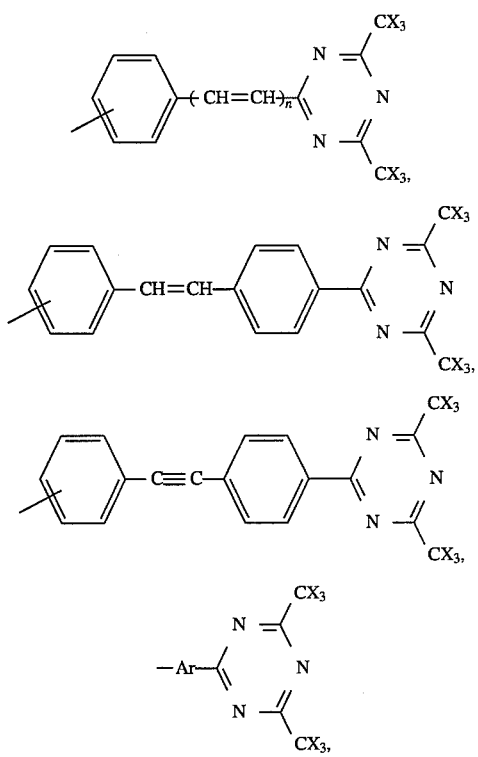

wherein X represents Cl or Br, n represents 1 or 2, and Ar represents an arylene group having up to 3 fused rings.

5. The photopolymerization initiator of claim 1, wherein $R^2(NCO)_2$ represents a member selected from the group consisting of tolylene-2,4-diisocyanate and isophorone diisocyanate.

6. The photopolymerization initiator of claim 1, wherein $R^3(OH)_x$ represents a member selected from the group consisting of (1) aliphatic alcohols and aliphatic polyols having from 1 to 20 carbon atoms; aralkyl alcohols and aralkyl polyols having up to 3 aromatic rings in the aryl portion thereof, and from 1 to 10 carbon atoms in the alkyl portion thereof; alkyl alcohols or alkyl polyols derived from heteroaromatic or heterocyclic compounds; (2) polyoxyethylene compounds selected from the group consisting of polyoxyethylene alkylphenols, polyoxyethylene alcohols, polyoxyethylene esters, polyoxyethylene alkylamines, polyoxyethylene alkylamides, block copolymers of polyoxyethylene and polyoxypropylene; (3) polyoxypropylene compounds selected from the group consisting of polyoxypropylene alkylphenols, polyoxypropylene alcohols, polyoxypropylene esters, polyoxypropylene alkylamines, polyoxypropylene alkylamides, block copolymers of polyoxypropylene and polyoxyethylene; and (4) glycols selected from the group consisting of polyethylene glycols, polypropylene glycols, polycaprolactone diols, acetylenic glycols, adducts of acetylenic glycol and ethylene oxide, and sulfopolyols.

7. The photopolymerization initiator of claim 6, wherein said chromophoresubstituted halomethyl-1,3,5-triazine photopolymerization initiator is selected from the group consisting of polyoxyethylene compounds and polyoxypropylene compounds having from 1 to 100 oxyalkylene groups per chromophore-substituted triazine unit.

8. The photopolymerization initiator of claim 1, wherein said chromophore-substituted halomethyl-1,3,5-triazine photopolymerization initiator has a molecular weight of from about 600 to about 5000 per each chromophore-substituted triazine unit.

9. The photopolymerization initiator of claim 2, wherein $R^1$ represents a member selected from the group consisting of

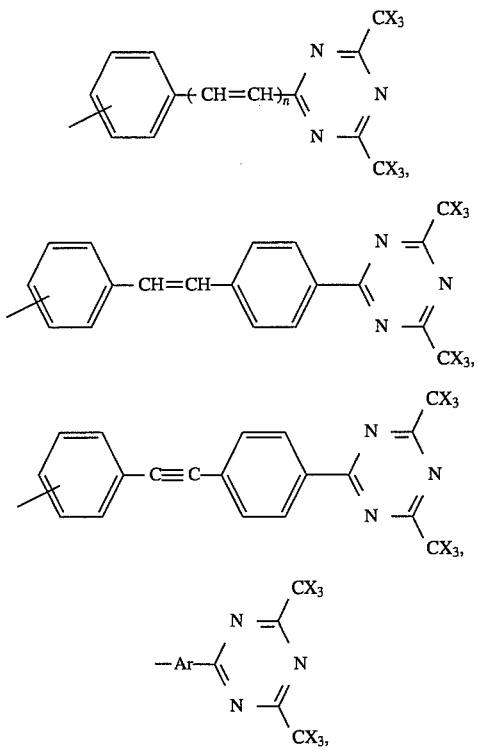

wherein X represents Cl or Br, n represents 1 or 2, and Ar represents an arylene group having up to 3 fused rings.

10. The photopolymerization initiator of claim 2, wherein $R^4$ represents a member selected from the group consisting of aromatic isocyanates; aliphatic isocyanates; arylaliphatic isocyanates; and polymeric isocyanates.

11. The photopolymerization initiator of claim 2, wherein said chromophoresubstituted halomethyl-1,3,5-triazine photopolymeriazation initiator has a molecular weight of from about 500 to about 5000 per each chromophore-substituted triazine unit.

12. The photopolymerization initiator of claim 3, wherein $R^5(CO_2H)_w$ represents a member selected from the group consisting of alkylene dicarboxylic acids; arylene carboxylic acids; compounds having carboxylic acid groups linked by combinations of aryl and alkyl groups; compounds having cyclic anhydride groups; and maleic anhydride copolymers.

13. The photopolymerization initiator of claim 3, wherein $R^1$ represents a member selected from the group consisting of

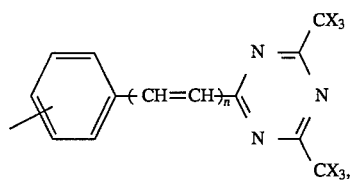

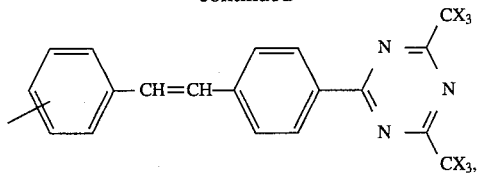
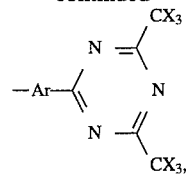
wherein X represents Cl or Br, n represents 1 or 2, and Ar represents an arylene group having up to 3 fused rings.
14. The photopolymerization initiator of claim 3, wherein said chromophore-substituted halomethyl-1,3,5-triazine photopolymerization initiator has molecular weight of from about 500 to about 5000 per each chromophore-substituted triazine unit.
* * * * *